United States Patent
Lin et al.

(10) Patent No.: US 9,205,073 B2
(45) Date of Patent: Dec. 8, 2015

(54) METHOD FOR TREATING VIRUS INFECTION USING DERIVATIVE OF ANILINE

(71) Applicant: CHINA MEDICAL UNIVERSITY, Taichung (TW)

(72) Inventors: Cheng-Wen Lin, Taichung (CN); An-Cheng Huang, Taichung (TW); Jin-Cherng Lien, Taichung (TW); Jia-Fong Ping, Taichung (TW); Shih-Wen Li, Taichung (TW); I-Chieh Chen, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 14/263,591

(22) Filed: Apr. 28, 2014

(65) Prior Publication Data

US 2015/0182491 A1    Jul. 2, 2015

(30) Foreign Application Priority Data

Jan. 2, 2014  (TW) .............................. 103100064 A

(51) Int. Cl.
| | | |
|---|---|---|
| A61K 31/34 | (2006.01) | |
| A61K 38/00 | (2006.01) | |
| A61K 31/341 | (2006.01) | |
| A61K 38/21 | (2006.01) | |

(52) U.S. Cl.
CPC .............. *A61K 31/341* (2013.01); *A61K 38/21* (2013.01); *A61K 38/215* (2013.01)

(58) Field of Classification Search
CPC .................................................. A61K 31/341
USPC .................................................. 514/472, 473
See application file for complete search history.

(56) References Cited

U.S. PATENT DOCUMENTS 4,845,122 A * 7/1989 Georgiev et al. .............. 514/472

FOREIGN PATENT DOCUMENTS

| WO | 2013/075596 A1 | 5/2013 |
|---|---|---|
| WO | 2013/180140 A1 | 12/2013 |

* cited by examiner

*Primary Examiner* — Shengjun Wang
(74) *Attorney, Agent, or Firm* — Ping Wang; Andrews Kurth LLP

(57) ABSTRACT

A method for treating a virus infection in a subject is provided. The method comprising administering to the subject in need an effective amount of a derivative of aniline selected from the group consisting of a compound of formula (I), a pharmaceutically acceptable salt of the compound of formula (I), a pharmaceutically acceptable ester of the compound of formula (I), and combinations thereof:

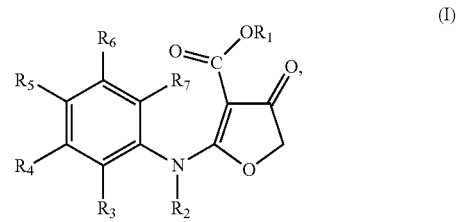

wherein,
$R_1$ is C1 to C10 alkyl;
$R_2$ is H or C1 to C4 alkyl; and
$R_3, R_4, R_5, R_6$ and $R_7$ are independently H, —OH, halogen, C1 to C10 alkyl, C1 to C10 alkoxyl, or (C1 to C10 alkylene)-O—O—(C1 to C10 alkyl).

13 Claims, 19 Drawing Sheets

METHOD FOR TREATING VIRUS INFECTION USING DERIVATIVE OF ANILINE

This application claims the benefit of Taiwanese Patent Application No. 103100064, filed on Jan. 2, 2014, in the Taiwan Intellectual Property Office, the disclosure of which is incorporated herein in its entirety by reference.

BACKGROUND OF THE INVENTION

1. Field of the Invention

The present invention relates to a method for treating a virus infection, comprising administering to a subject in need a derivative of aniline. In particular, the method of the present invention is effective in inhibiting virus-induced apoptosis, inhibiting virus-induced cytopathic effect, and/or inhibiting viral replication in a virus-infected cell. The method of the present invention may further comprise administering to the subject an interferon to provide a synergistic effect in treating a virus infection.

2. Descriptions of the Related Art

A virus is non-cellular and consists of genetic materials (DNA or RNA) and protein coats (some viruses can form an envelope of lipids that surrounds the protein coat when they reach the surface of host cells). A virus is a segment of DNA or RNA coated by a protective coat. A virus cannot reproduce by itself due to its simple composition. Virus replication is conducted by using the system of a host cell through an infection mechanism to synthesize and assemble various viral proteins and viral nucleic acids. The replication cycle of a virus through a virus-infected cell can be classified into approximately six steps as follows: attachment, invasion, uncoating, synthesis, packaging and release.

It has been known that the gene structure and replication cycle of viruses in the same genus are very similar. For example, the genome of *Flavivirus* genus virus is a positive single strand RNA. The complete genome is about 11 kilobases (kb) in length. There is high conservation between gene sequences in the genome. For example, the 5'-end of the genomic RNA has a Type I cap, the 3'-end of the genomic RNA lacks a poly A tail, and each of the 5' and 3' ends of the genomic RNA has an untranslated region (UTR), which can form a highly conserved secondary structure. There is a big open reading frame (ORF) between these two UTRs. The ORF can be translated into a polypepetide which can sequentially generate three structural proteins (i.e., core protein, pre-membrane protein, envelope protein) and seven non-structural proteins, NS1, NS2A, NS2B, NS3, NS4A, NS4B, and NS5. The viral particles of the *Flavivirus* genus virus can bind to the receptors on a host cell by its envelope proteins to enter the host cell through a receptor-mediated endocytosis, and then change the structure of the envelope proteins by an endosome acidification to conduct a membrane fusion with the endosome of the host cell, thereby releasing viral RNA genome into the cytosol of the host cell. The protein translation of the viral genome will then be directly conducted in the host cells to generate a long chain polyprotein which will be cleaved by signalases in the endoplasmic reticulum (ER) and viral NS2BNS3 protease, thereby generating the aforementioned three structural proteins and seven non-structural proteins. The viral genome is replicated and assembled with the viral proteins that have gathered in the ER to from a viral particle. The viral particle is then transported into the Golgi body and released from the virus-infected cell through exocytosis.

The *Enterovirus* genus virus is a positive single strand RNA. The complete genome is about 7.4 kb in length. There is high conservation between gene sequences in the genome. For example, VPg-5'-NCR, VP0 (VP4, VP2), VP3, VP1, VP2A, VP2B, VP2C, VP3A, VP3B, VP3C, VP3D and a poly A tail connected to 3'-end are presented sequentially, from the 5'-end to the 3'-end of the genomic RNA. VP0 is a precursor of VP4 and VP2 before separation. VP1, VP2, VP3 and VP4 are structural proteins of *enterovirus*, which relates to the characteristics of the virus infection in a host cell. Among these structural proteins, VP1, VP2 and VP3 are the primary proteins for composing a viral capsid, and VP1 also relates to the binding of cell receptors. When the viral particles of *Enterovirus* genus virus can bind to the receptors on the surface of a host cell, the N-terminal of viral protein VP1 will change structurally. VP1 will shift from the inside to the outside of the virion and form a channel with the receptors of host cells, thereby leading the viral genomic RNA to enter into a host cell. Then, the viral genomic RNA will be translated into multi proteins and cleaved by viral proteins such as VP2A, VP3C and VP3CD, to generate a viral outer sheath protein and a RNA polymerase, to accomplish the replication of the viral genomic RNA and form a new viral particle with infectious ability.

It has been known that some viruses in the *Flavivirus* genus, such as tick-borne encephalitis virus (TBEV), West Nile virus (WNV), yellow fever virus (YFV), Japanese encephalitis virus (JEV), and dengue virus (DEN) cause serious human diseases. The diseases caused by Japanese encephalitis virus or dengue virus are the most severe. Japanese encephalitis virus is transmitted through mosquito bites. Japanese encephalitis virus infection will cause acute cerebral meningitis (also referred to as "Japanese encephalitis"), leading to damage to the brain, spinal cord and meninges. The transmission of Japanese encephalitis virus usually occurs in summer and it is endemic in Southeast Asia, including Siberia, India, China, Taiwan, Japan, Korea, Philippine, Thailand. There are about 30,000 to 50,000 confirmed cases annually. The transmission of Japanese encephalitis virus in Taiwan occurs annually between May and October, and it usually peaks in July. The death rate ranges from 30% to 70%, especially when the severe state is reached, such as aseptic meningitis and respiratory failure. The death rate is especially high among children under 6 years of age and persons with a weak immune system over 65 years of age. A full-scale vaccination is only available in Taiwan, Japan, Korea, Thailand and Singapore. There are no specific drugs that can be used for treatment to date. In addition to supportive therapies, the only treatment that is used in clinics is a combination of an anti-virus drug, Ribavirin, and interferon. However, the prognosis is poor, and such treatment usually results in severe sequelae.

Dengue virus can be classified into four antigenically distinct serotypes: Type 1, Type 2, Type 3 and Type 4. Patients infected with dengue virus show symptoms such as sudden onset of high fever ($\geq 38°$ C.), headache, retro-orbital pain, muscle pain, joint pain, and exanthema, which is referred to as "typical dengue fever." Moreover, when being infected with different types of dengue virus, it has a higher probability of becoming "dengue hemorrhagic fever." In addition to the aforementioned symptoms of typical dengue fever, dengue hemorrhagic fever can cause hemorrhaging. The incidence rate is especially high among children under 15 years of age. If not treated immediately, hyper-plasma leakage that is caused by severe hemorrhage may lead to shock or death. The death rate can be up to 50%. Dengue fever usually occurs in warmer seasons (i.e., May to October), and it is endemic in all areas of the world with subtropical climates (i.e., areas between northern latitude of 25 degrees and southern latitude of 25 degrees), including 61 countries. About 1.5 billion people live in a risk of dengue transmission. Between 1970 and 1980, there were about 250,000 infections of dengue hemorrhagic fever yearly. Dengue fever has been transmitted worldwide since the 1980's. There is no vaccine that can be used to date, and the only treatment is supportive therapy but not specific drugs.

The *Enterovirus* genus virus includes 23 types of group A coxsackievirus (CVA), 6 types of group B coxsackievirus (CVB), 3 types of poliovirus, 30 types of echovirus, and *enterovirus* types 68 to 71 (EV68 to EV71). The *Enterovirus* mainly infects children under 3 years of age, and is usually transmitted in the summer and fall. Persons infected with the *enterovirus* may have minor symptoms like a common cold, such as hand-foot-mouth disease and herpangina. Sometimes, an *enterovirus* infection may lead to special clinical manifestations, such as aseptic meningitis, viral encephalitis, myocarditis, paralysis syndrome, and acute hemorrhagic conjunctivitis. Since 1990, infectious cases have occurred in Taiwan, Hong Kong, China, Japan, Malaysia, Singapore and Macao. The cases of *enterovirus* infection are found all year round in Taiwan. Peak season is between April and September. In 1998, there was a largest outbreak of 130,000 cases of hand-foot-mouth disease and herpangina caused by EV71 and coxsackievirus A16 (CAV16). Most of the cases were reported between May and July and between September and November, including 400 cases with severe syndrome and 78 cases of death. There are no specific drugs to treat an *enterovirus* infection, especially EV71. Only supportive therapy can be used depending on the symptoms. There is one vaccine that is being developed in Taiwan, but it is still in phase II of the clinical trial, which is at least 4 to 5 years from clinical use. Furthermore, because there are over 100 types of *enterovirus*, it is unknown whether a single vaccine can be used to treat several kinds of *enterovirus*. In addition, some pharmaceutical companies now are in the process of investigating the drugs which can inhibit *enterovirus*. However, all of these drugs are still in undergoing clinical trials and thus, the safety in children cannot be thoroughly evaluated.

There is still a necessity and urgency for developing a drug for effectively treating a virus infection because supportive therapy is not sufficient The inventors of the present invention found that the compound of formula (I) of the present invention can effectively inhibit virus-induced apoptosis, inhibit virus-induced cytopathic effect, and inhibit virus replication in a virus-infected cell. Furthermore, the compound of formula (I) can be used in combination with an interferon simultaneously or sequentially to generate a synergistic effect on treating a virus infection. In particular, the compound of formula (I) of the present invention can generate the aforementioned effects on *Flavivirus* genus virus and *Enterovirus* genus virus, especially on Japanese encephalitis virus, dengue virus and/or *enterovirus* type 71.

SUMMARY OF THE INVENTION

An objective of the present invention is to provide a use of a derivative of aniline in the manufacture of a medicament for treating a virus infection, wherein the derivative of aniline is selected from the group consisting of a compound of formula (I), a pharmaceutically acceptable salt of the compound of formula (I), a pharmaceutically acceptable ester of the compound of formula (I), and combinations thereof:

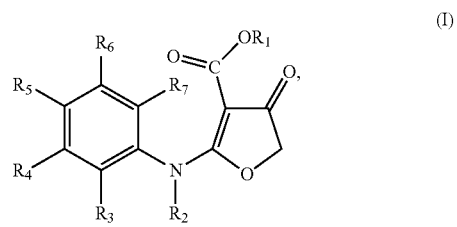

wherein, $R_1$ is C1 to C10 alkyl; $R_2$ is H or C1 to C4 alkyl; and $R_3$, $R_4$, $R_5$, $R_6$ and $R_7$ are independently H, —OH, halogen, C1 to C10 alkyl, C1 to C10 alkoxyl, or (C1 to C10 alkylene)-O—O—(C1 to C10 alkyl). Preferably, $R_1$ is C1 to C6 alkyl; $R_2$ is H; and $R_3$, $R_4$, $R_5$, $R_6$ and $R_7$ are independently H, —OH, halogen, C1 to C4 alkyl, C1 to C4 alkoxyl, or (C1 to C4 alkylene)-O—O—(C1 to C6 alkyl). More preferably, $R_1$ is C1 to C6 alkyl; $R_2$ is H; and $R_3$, $R_4$, $R_5$, $R_6$ and $R_7$ are independently H or C1 to C4 alkyl.

Another objective of the present invention is to provide a method for treating a virus infection in a subject, comprising administering to the subject in need an effective amount of the aforesaid derivative of aniline.

Yet another objective of the present invention is to provide a pharmaceutical composition for treating a virus infection, comprising the aforesaid derivative of aniline.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIGS. 6A and 6B are statistical bar diagrams showing the replication of JEV T1P1 in TE671 cells which have been infected with JEV T1P1 for 36 hours (FIG. 6A) or 48 hours (FIG. 6B) (*p<0.005: represents a statistical significance; **p<0.001: represents a statistical significance), wherein the vertical axis represents the virus titer, the upper row of horizontal axis represents there is a JEV T1P1 infection (+); and the lower row of the horizontal axis represents the concentration of compound (1);

DESCRIPTION OF THE PREFERRED EMBODIMENT

Figure 1A:
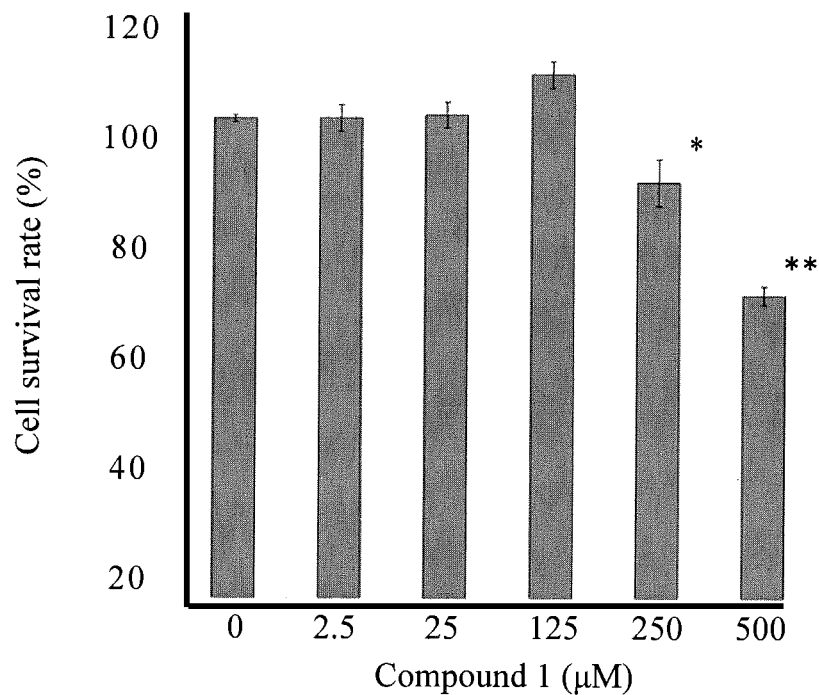
FIGS. 1A to 1C are statistical bar diagrams showing the survival rates of BHK-21 cells, TE671 cells and RD cells treated by compound (1) exemplified in Example 1 (*$p<0.005$: represents a statistical significance; **$p<0.001$: represents a statistical significance), wherein the vertical axis represents the survival rate of cells and the horizontal axis represents the concentration of compound (1)

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the," or the like recited in the specification of the present invention (especially in the claims) should include both the singular and plural forms. Furthermore, the term "effective amount" or "amount effective for treatment" used in this specification refers to the amount of the compound that can at least partially alleviate the condition that is being treated in a suspected subject when administered to the subject in need. The term "subject" used in this specification refers to a mammalian, including human and non-human animals.

Unless otherwise state herein, the term a "derivative of aniline of formula (I)" used in this specification includes a derivative of aniline of formula (I), a pharmaceutically acceptable salt of the derivative of aniline of formula (I), a pharmaceutically acceptable ester of the derivative of aniline of formula (I), and combinations thereof.

Generally, after being infected by a virus, the virus-infected cells will usually secrete an interferon, especially a type I interferon, to activate the immune system-related signaling pathway, comprising the Janus kinase-signal transducer and activator of transcription (JAK-STAT) signaling pathway, the protein kinase AkT-mammalian target of rapamycin (AkT-mTOR) signaling pathway, and the extracellular signal-regulated kinase-cAMP response element-binding protein (ERK-CREB) signaling pathway, thereby promoting a virus-infected cell to generate anti-virus proteins and induce an immune response to defend viral invasion. However, the virus can integrate itself into the genome of a virus-infected cell to control the genetic material of the virus-infected cell, and can synthesize various viral proteins and viral nucleic acids needed for its replication by using the materials and enzymes of the virus-infected cell, so as to inhibit the activation of an immune-related signaling pathway, thereby, escaping clearance by the immune system of the virus-infected cell.

The inventors of the present invention found that the derivative of aniline of formula (I) as below has an ability of inhibiting virus-induced apoptosis, virus-induced cytopathic effect, and/or virus replication in a virus-infected cell, and can be used in combination with an interferon simultaneously or sequentially to generate a synergistic effect on treating a virus infection:

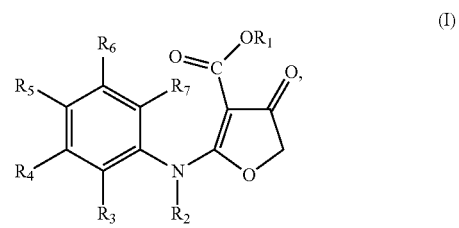

(I)

wherein, $R_1$ is C1 to C10 alkyl; $R_2$ is H or C1 to C4 alkyl; and $R_3$, $R_4$, $R_5$, $R_6$ and $R_7$ are independently H, —OH, halogen, C1 to C10 alkyl, C1 to C10 alkoxyl, or (C1 to C10 alkylene)-O—O—(C1 to C10) alkyl.

Accordingly, the present invention provides the applications of a derivative of aniline, comprising the use of a derivative of aniline in the manufacture of a medicament for treating a virus infection, administering to a subject in need a derivative of aniline to treat a virus infection, and providing a pharmaceutical composition comprising a derivative of aniline, wherein the derivative of aniline is selected from the group consisting of a compound of formula (I), a pharmaceutically acceptable salt of the compound of formula (I), a pharmaceutically acceptable ester of the compound of formula (I), and combinations thereof:

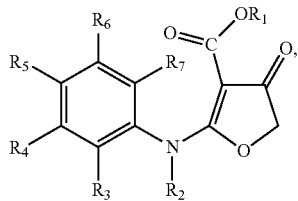

(I)

wherein, $R_1$ is C1 to C10 alkyl; $R_2$ is H or C1 to C4 alkyl; and $R_3$, $R_4$, $R_5$, $R_6$ and $R_7$ are independently H, —OH, halogen, C1 to C10 alkyl, C1 to C10 alkoxyl, or (C1 to C10 alkylene)-O—O—(C1 to C10 alkyl).

The derivative of aniline of formula (I) used in the present invention can be prepared from the reaction of a corresponding aniline. For example, when $R_2$ is H, the compound of formula (I) can be provided through the following reactions:

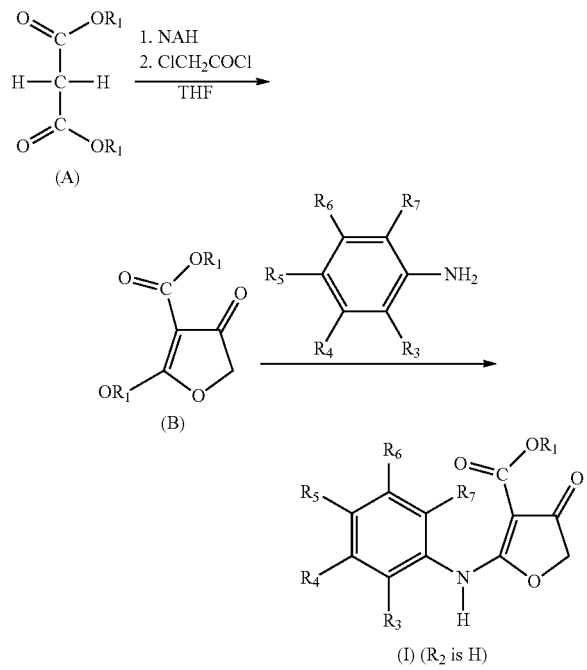

As illustrated by the above synthesis scheme, a suspension of sodium hydride (NaH) in dry tetrahydrofuran (THF) was prepared, compound (A) with a substituent $R_1$ corresponding to the desired derivative of aniline was added into the suspension (for example, when $R_1$ in the desired derivative of aniline is ethyl, the compound (A) is diethyl malonate), and then chloroacetyl chloride (ClCH$_2$COCl) was added to carry out a cyclization reaction and produce an intermediate compound (B) (for example, when $R_1$ in the desired derivative of aniline is ethyl, the reaction product of the cyclization reaction, compound (B) is ethyl 2-ethoxy-4-oxo-4,5-dihydrofuran-3-carboxylate). Then, an optionally substituted aniline was added to carry out a condensation reaction to provide the corresponding, desired derivative of aniline of formula (I).

Preferably, the derivative of aniline used in the present invention is a compound of formula (I), $R_1$ is C1 to C6 alkyl; $R_2$ is H; and $R_3$, $R_4$, $R_5$, $R_6$ and $R_7$ are independently H, —OH, halogen, C1 to C4 alkyl, C1 to C4 alkoxyl, or (C1 to C4 alkylene)-O—O—(C1 to C6 alkyl). More preferably, in formula (I), $R_1$ is C1 to C6 alkyl; $R_2$ is H; and $R_3$, $R_4$, $R_5$, $R_6$ and $R_7$ are independently H or C1 to C4 alkyl.

Embodiments of the derivative of aniline of formula (I) used in the present invention include but are not limited to the following compounds:

(1) ethyl 2-(3',5'-dimethylanilino)-4-oxo-4,5-dihydrofuran-3-carboxylate;
(2) ethyl 2-(3'-methoxyanilino)-4-oxo-4,5-dihydrofuran-3-carboxylate;
(3) ethyl 2-(2'-methyl-4'-chloro-anilino)-4-oxo-4,5-dihydrofuran-3-carboxylate;
(4) ethyl 2-(2'-ethoxycarbonylmethylanilino)-4-oxo-4,5-dihydrofuran-3-carboxylate;
(5) ethyl 2-(3',4',5'-trimethroxyanilino)-4-oxo-4,5-dihydrofuran-3-carboxylate;
(6) ethyl 2-(3'-hydroxyanilino)-4-oxo-4,5-dihydrofuran-3-carboxylate;
(7) ethyl 2-(3'-chloroanilino)-4-oxo-4,5-dihydrofuran-3-carboxylate;
(8) ethyl 2-(3',5'-dimethoxyanilino)-4-oxo-4,5-dihydrofuran-3-carboxylate;
(9) ethyl 2-anilino-4-oxo-4,5-dihydrofuran-3-carboxylate; and
(10) ethyl 2-(3',4'-dimethylanilino)-4-oxo-4,5-dihydrofuran-3-carboxylate.

In some embodiments of the present invention, ethyl 2-(3',5'-dimethylanilino)-4-oxo-4,5-dihydrofuran-3-carboxylate was used as the derivative of aniline of formula (I).

It has been found that the derivative of aniline of formula (I) of the present invention can effectively inhibit virus-induced apoptosis, inhibit virus-induced cytopathic effect, and/or inhibit virus replication in a virus-infected cell.

Specifically, the derivative of aniline of formula (I) of the present invention can effectively activate the virus-suppressed signaling pathway in a virus-infected cell including such as but not limited to activating a virus-suppressed JAK-STAT signaling pathway in a virus-infected cell, activating a virus-suppressed AkT-mTOR signaling pathway in a virus-infected cell, and activating a virus-suppressed ERK-CREB signaling pathway in a virus-infected cell.

In addition, the derivative of aniline of formula (I) of the present invention also can effectively promote the expressions of anti-virus genes in a virus-infected cell. Examples of the anti-virus genes include an interferon, an interferon receptor, an interferon regulatory factor, protein kinase R (PKR), and oligoadenylate synthetase (OAS). The examples of the interferon include interferon-α (IFN-α) and interferon-β (IFN-β). Examples of the interferon receptor include interferon-α receptor-1 (IFNAR1). Examples of the interferon regulatory factor include interferon regulatory factor-3 (IRF-3) and interferon regulatory factor-7 (IRF-7).

In some embodiments of the present invention, the derivative of aniline of formula (I) was used to treat diseases caused by the *Flavivirus* genus virus. Among viruses in the *Flavivirus* genus, viruses such as tick-borne encephalitis virus (TBEV), West Nile virus (WNV), yellow fever virus (YFV), Japanese encephalitis virus (JEV), and dengue virus (DEN) had ever caused serious human diseases. The derivative of aniline of formula (I) of the present invention is especially effective in treating the infection caused by Japanese encephalitis virus and dengue virus (especially dengue virus type 2).

In some other embodiments of the present invention, the derivative of aniline of formula (I) was used to treat diseases caused by the *Enterovirus* genus virus. The *Enterovirus* genus virus includes 23 types of group A coxsackievirus (CVA), 6 types of group B coxsackievirus (CVB), 3 types of poliovirus, 30 types of echovirus, and *enterovirus* types 68 to 71 (EV68 to EV71). The derivative of aniline of formula (I) of the present invention can especially effectively treat *enterovirus* type 71 (EV71).

For treating a virus infection, the derivative of aniline of formula (I) of the present invention can be used in combination with an interferon simultaneously or sequentially to provide a synergistic effect. Examples of the interferon include, but not limited to, IFN-α and IFN-β. In an embodiment of the present invention, the derivative of aniline of formula (I) was used in combination with IFN-β simultaneously. The aforesaid synergistic action was especially effective in treating *enterovirus* infection, particular in treating an EV71 infection.

The derivative of aniline of formula (I) of the present invention can be used to provide a pharmaceutical composition for treating a virus infection or be used to manufacture a medicament for treating a virus infection, especially a pharmaceutical composition or medicament for treating the aforementioned virus infections. The pharmaceutical composition or medicament can be manufactured into any form, and can be administered in any suitable form. For example, the medicament can be administered by oral, subcutaneous, nasal or intravenous to a subject in need, but is not limited thereby. Depending on the form and purpose, the pharmaceutical composition or medicament can further comprise a pharmaceutically acceptable carrier.

For oral administration, the pharmaceutical composition provided by or the medicament manufactured by using the derivative of aniline of formula (I) of the present invention can comprise a pharmaceutically acceptable carrier that would not adversely affect the desired activity of the derivative of aniline of formula (I). The carrier includes such as solvents, oily solvents, diluents, stabilizers, absorption retarders, disintegrants, emulsifiers, antioxidants, adhesives, lubricants, moisture absorbents, etc. The medicament or pharmaceutical composition can be provided in any suitable form for oral administration, such as a tablet, a capsule, a granule, a powder, a fluid extract, a solution, syrup, a suspension, an emulsion, a tincture, etc.

For subcutaneous or intravenous administration, the pharmaceutical composition provided by or the medicament manufactured by using the derivative of aniline of formula (I) of the present invention can comprise one or more component(s), such as an isotonic solution, a saline buffer solution (e.g., a phosphate buffer solution or a citrate buffer solution), a solubilizer, an emulsifier, other carriers, etc., to provide the pharmaceutical composition or medicament as an intravenous injection, an emulsion intravenous injection, a powder injection, a suspension injection, or a powder-suspension injection.

Optionally, the medicament manufactured by or the pharmaceutical composition provided by using the derivative of aniline of formula (I) of the present invention may comprise other a flavoring agent, a toner, a coloring agent to enhance the taste and visual appeal of the resultant medicament or composition. A suitable amount of a preservative, a conservative, an antiseptic, an anti-fungus reagent, and etc., may also be added to improve the storability of the resultant pharmaceutical composition or medicament. In addition, the pharmaceutical composition or medicament may further comprise one or more active components or be used in combination with a medicament comprising the one or more other active components to further enhance the effects of the pharmaceutical composition or medicament or to increase the application flexibility and adaptability of the formulation thus provided, as long as the other active components have no adverse effect on the desired effect of the derivative of aniline of formula (I). For example, the active component can be an interferon (e.g., IFN-α or IFN-β), an antioxidant (e.g., vitamin E), or an immune modulator, etc. In one embodiment of the present invention, an interferon was further comprised in the pharmaceutical composition or medicament to treat an *enterovirus* infection. For example, IFN-β was further comprised in the pharmaceutical composition or medicament to treat an EV71 infection.

Depending on the requirements of the subject, the medicament manufactured by or the pharmaceutical composition provided by using the derivative of aniline of formula (I) of the present invention, can be applied with various administration frequencies, such as once a day, several times a day or once for days, etc. For example, when applied to the human body for treating a Japanese encephalitis virus infection, the dosage of the pharmaceutical composition or medicament is about 15 mg (as the compound of formula (I))/kg-body weight to about 35 mg (as the compound of formula (I))/kg-body weight per day, and preferably is about 20 mg (as the compound of formula (I))/kg-body weight to about 25 mg (as the compound of formula (I))/kg-body weight per day, wherein the unit "mg/kg-body weight" means the dosage required per kg-body weight of the treated subject. However, for patients with acute conditions, the dosage can be increased to several times or several tens of times, depending on the practical requirements. For example, in the use of ethyl 2-(3',5'-dimethylanilino)-4-oxo-4,5-dihydrofuran-3-carboxylate for manufacturing a medicament for treating a virus infection, the dosage of medicament may be about 25 mg (as 2-(3',5'-dimethylanilino)-4-oxo-4,5-dihydrofuran-3-carboxylate)/kg-body weight.

The present invention also provides a method for treating a virus infection in a subject in need, comprising administering to the subject an effective amount of a derivative of aniline selected from the group consisting of a compound of formula (I), a pharmaceutically acceptable salt of the compound of formula (I), a pharmaceutically acceptable ester of the compound of formula (I), and combinations thereof. The selection of the derivative of aniline, and the form and dosage for administering thereof are all in line with the above descriptions.

The present invention will be further illustrated in detail with specific examples as follows. However, the following examples are provided only for illustrating the present invention, and the scope of the present invention is not limited thereby.

EXAMPLE 1

Preparation of the Compound of Formula (I)

(A) Synthesis of 2-(3',5'-dimethylanilino)-4-oxo-4,5-dihydrofuran-3-carboxylate (compound 1)

A suspension of NaH (60%, 8.0 g, 0.2 mole) in dry THF (40 ml) was prepared, and a mixture of diethyl malonate (32.0 g, 0.2 mole) and THF (50 ml) was added dropwise into the suspension to provide a mixture. The mixture was cooled to 10 to 12° C. A solution of ClCH$_2$COCl (11.3 g, 0.1 mole) in THF (100 ml) was added dropwise into the mixture. Then, the mixture was kept at a low temperature of 10 to 12° C. for 1 hour, warmed by warm water (40 to 45° C.) for about 1 hour, and then cooled to 10 to 12° C. A solution of 3,5-dimethylaniline (12.1 g, 0.1 mole) in THF (50 ml) was added dropwise into the above mixture, and then stirred at room temperature for 1 hour and heated on the water bath for several hours. The obtained reaction solution was examined by TLC to determine whether the reaction was completed. Then, the reaction solution was vacuum concentrated to remove most of the THF to obtain a residue, which is a yellow viscous substance. The yellow viscous substance was placed in a flask, and ice water (600 ml) and n-hexane (300 ml) were poured thereinto. The flask was shaken vigorously and precipitates were observed. The precipitates were filtrated and collected by a Büchner funnel, and washed once by n-hexane (100 ml) and little ethanol, respectively. The obtained residue was heated and dissolved in 125 ml of ethanol. The solution was then filtrated to remove the un-dissolved impurities as it was still hot. The filtrate was left to sit until crystallization occurred. The crystals were collected and recrystallized by ethanol. 21.74 g of the crystal block was obtained. The productivity was 79% and the melting point of the crystal ranged from 144 to 147° C. The data of the optical spectrum was as follows: MS (m/z): 275 (M$^+$), IR (KBr disc) cm$^{-1}$: 3251.5 (—NH—), 1708.6 (C$_4$=O), 1662.8 (C$_3$—CO-OEt); UV$\lambda_{max}$ nm (CHCl$_3$)(log ε): 283 (4.45); $^1$H-NMR (200 MHz, CDCl$_3$) δ: 1.240 (3H, t, J=7.0 Hz, H-2"), 2.256 (6H, s, C$_{3'}$—C$\underline{H}_3$, C$_{5'}$—C$\underline{H}_3$), 4.202 (2H, q, J=7.0 Hz, H-1"), 4.67 (2H, s, H-5), 6.88 (1H, s, H-4'), 7.05 (2H, s, H-2', H-6'), 10.127 (1H, s, NH); $^{13}$C-NMR (200 MHz, DMSO-d$_6$) δ: 14.62 (C-2"), 21.04 (3'-$\underline{C}$H3, 5'-$\underline{C}$H3), 59.41 (C-1"), 75.41 (C-5), 86.85 (C-3), 120.58 (C-2', C-6'), 127.73 (C-4'), 135.03 (C-1'), 135.03 (C-3', C-5'), 164.32 (C-2), 177.25 (C-3"), 188.65 (C-4).

(B) Synthesis of ethyl 2-(3'-methoxyanilino)-4-oxo-4,5-dihydrofuran-3-carboxylate (compound 2)

The preparation procedures of compound 1 were repeated except that 3'-methoxyaniline (10.71 g, 0.1 mole) was substituted for 3,5-dimethylaniline. 21.6 g of white acicular crystal was obtained. The productivity was 78% and the melting point of the crystal was 140.7° C. The data of optical spectrum was as follows: MS (m/z, %): 278 (M$^+$+1, 9.12), 277 (M$^+$, 53.04), 231 (M$^+$-46, 100); IR (KBr disc) cm$^{-1}$: 3282 (—NH—), 1703.14 (C$_4$=O), 1662.47 (C$_3$—CO-OEt); UV$\lambda_{max}$ nm (MeOH)(log ε): 283.0 (4.218); $^1$H-NMR (200 MHz, CDCl$_3$) δ: 1.32 (3H, t, J=6.9 Hz, H-2"), 3.75 (3H, s, 3'-OC$\underline{H}_3$), 4.30 (2H, q, J=6.9 Hz, H-1"), 4.61 (2H, s, H-5), 6.7~7.25 (4H, m, H-2', H-4', H-5', H-6'), 10.2 (1H, s, —N$\underline{H}$—); $^{13}$C-NMR (200 MHz, CDCl$_3$) δ: 14.22 (C-2"), 55.15 (3'-O$\underline{C}$H$_3$), 60.28 (C-1"), 75.21 (C-5), 87.39 (C-3), 107.15 (C-2'), 111.08 (C-4' 113.24 (C-6'), 129.96 (C-5'), 135.62 (C-1'), 160.05 (C-3'), 165.26 (C-2), 177.34 (C-3"), 188.12 (C-4).

(C) Synthesis of ethyl 2-(2'-methyl-4'-chloro-anilino)-4-oxo-4,5-dihydrofuran-3-carboxylate (compound 3)

The preparation procedures of compound 1 were repeated except that 2'-methyl-4'-chloro-aniline (10.71 g, 0.1 mole) was substituted for 3,5-dimethylaniline. 18.55 g of white crystal was obtained. The melting point of the crystal ranged from 118 to 119° C. The data of the optical spectrum was as follows: MS (m/z) 262 (M$^+$+1, 8.81), 261 (M+, 40.95); IR (KBr disc) cm$^{-1}$ 3169.35 (—NH—), 1703.62 (C4=O), 1651.96 (C3-CO-OEt); UV$\lambda_{max}$ nm (MeOH)(log ε): 294.5 (4.1717); $^1$H-NMR (200 MHz, DMSO-d$_6$) δ: 1.245 (3H, t, J=7 Hz, H-2"), 2.29 (3H, s, 2'-CH3), 4.035 (2H, q, J=7 Hz, H-1"), 4.62 (2H, s, H-2), 7.208-7.447 (4H, m, H-3', H-4', H-5', H-6'), 10.15 (1H, s, —NH—); $^{13}$C-NMR (200 MHz, DMSO-d$_6$) δ: 14.69 (C-2"), 17.65 (2'-$\underline{C}$H3), 59.32 (C-1"), 75.24 (C-5), 86.67 (C-3), 125.46 (C-6'), 126.77 (C-4'), 127.27 (C-5'), 130.68 (C-3'), 132.68 (C-2'), 133.92 (C-1'), 164.28 (C-2), 177.60 (C-3"), 188.81 (C-4).

(D) Synthesis of ethyl 2-(2'-ethoxycarbonylmethylanilino)-4-oxo-4,5-dihydrofuran-3-carboxylate (compound 4)

(a) Preparation of ethyl 2-(2'-aminophenyl)acetate 2-(2'-nitrophenyl) acetic acid (18.1 g, 0.1 mole) was dissolved in a 95% ethanol solution (200 ml), kept at a low temperature of 8° C., and then 98% HCl (20 ml) was slowly added dropwise thereinto to provide a mixture. The mixture was stirred for 1 hour, heated and reflux on a water bath for 4 hours, and then stirred at room temperature for 1 to 2 days. The obtained reaction solution was examined by TLC to determine whether the reaction was complete. Then, the reaction solution was vacuum concentrated to remove ethanol solution. The residues were slowly added with ice water, and then extracted by CHCl$_3$ for several times. The obtained extract was dried by adding dry MgSO$_4$, and vacuum concentrated to remove CHCl$_3$ to obtain a massive yellow coagulum, 2-(2'-nitrophenyl) acetate (16.9 g, productivity: 81%).

2-(2'-nitrophenyl)acetate (10.5 g, 0.1 mole) was placed in a tempered glass flask with 50 ml of added ethanol and 10% palladium/carbon mixture (1.0 g) as a catalyst. The aforesaid reaction solution was placed into a hydrogenator for hydrogenation. The obtained reaction solution was examined by TLC to determine whether the reaction was complete. After the reaction was completed, the reaction solution was filtrated to remove the palladium/carbon mixture and then vacuum concentrated to remove ethanol to obtain a brown-yellow viscous liquid, ethyl 2-(2'-aminophenyl)acetate.

(b) Preparation of ethyl 2-(2'-ethoxycarbonylmethylanilino)-4-oxo-4,5-dihydrofuran-3-carboxylate A suspension of NaH (60%, 8.0 g, 0.2 mole) in dry THF (40 ml) was prepared, and a mixture of diethyl malonate (32.0 g, 0.2 mole) and THF (50 ml) was slowly added into the suspension to provide a mixture. The mixture was cooled to 10 to 12° C., and a solution of ClCH$_2$COCl (11.3 g, 0.1 mole) in THF (100 ml) was added dropwise thereinto. Then, the reaction solution was kept at 10 to 12° C. for 1 hour, warmed by warm water (40 to 45° C.) for about 1 hour, and then cooled to 10 to 12° C. A solution of the ethyl 2-(2'-aminophenyl)acetate (0.1 mole) prepared in step (a) in THF (50 ml) was added dropwise into the above reaction solution, and then stirred at room temperature for 1 hour and heated on a water bath for several hours. The obtained reaction solution was examined by TLC to determine whether the reaction was complete. Then, the reaction solution was vacuum concentrated to remove most of the THF. Ice water (600 ml) was poured into the vacuum concentration flask. Then, the reaction solution in the vacuum concentration flask was extracted by CHCl$_3$ several times. The obtained extract was washed by water and dried by dry MgSO$_4$, and vacuum concentrated to remove CHCl₃. The concentrated liquid was placed at room temperature for crystallization. The crystal was collected and recrystallized by ethanol to obtain 13.66 g of a white acicular crystal. The productivity was 41% and the melting point of the crystal was 91.2° C. The data of the optical spectrum was as follows: MS (m/z, %): 332.8 (M⁺, 35.85), 333.8 (M⁺+1, 7.73); IR (KBr disc) cm⁻¹: 3121.86 (—NH—), 1737.28 (C8'=O), 1698.3 (C4=O), 1664.19 (C3-CO-OEt); UV$\lambda_{max}$ nm (MeOH) (log ε): 291.0 (3.825); ¹H-NMR (200 MHz, DMSO-d₆) δ: 1.176 (3H, t, J=7 Hz, H-10'), 1.23 (3H, t, 166J=7 Hz, H-2''), 3.763 (2H, s, H-7'), 4.049 (2H, q, J=7 Hz, H-9'), 4.192 (2H, q, J=7 Hz, H-2''), 4.573 (2H, s, H-5), 7.321~7.453 (4H, m, H-3', H-4', H-5', H-6'), 10.115 (1H, s, NH); ¹³C-NMR (200 MHz, DMSO-d₆) δ: 14.09 (C-10'), 14.65 (C-2''), 37.29 (C-7'), 56.30 (C-1''), 60.96 (C-9'), 75.17 (C-5'), 86.93 (C-3), 126.79 (C-6'), 127.64 (C-4'), 128.17 (C-2'), 130.33 (C-3'), 131.44 (C-5'), 134.03 (C-1'), 164.09 (C-2), 170.88 (C-8'), 177.90 (C-3''), 188.98 (C-4).

(E) Synthesis of Others Derivative of Aniline (Compounds 5 to 10)

The preparation procedures of compound 1 were repeated except that various optionally substituted anilines (0.1 mole) were substituted for 3,5-dimethylaniline, to obtain corresponding compounds of formula (I) (i.e., compounds 5 to 10 as shown in Table 1):

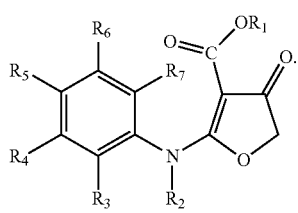

(I)

TABLE 1

| compound | optionally substituted aniline | R₂ | R₃ | R₄ | R₅ | R₆ | R₇ | mp (° C.) |
|---|---|---|---|---|---|---|---|---|
| 5 | 3',4',5'-trimethroxyaniline | H | H | OCH₃ | OCH₃ | OCH₃ | H | 163.3 |
| 6 | 3'-hydroxyaniline | H | H | OH | H | H | H | 210-211 |
| 7 | 3'-chloroaniline | H | H | Cl | H | H | H | 159.5 |
| 8 | 3',5'-dimethoxyaniline | H | H | OCH₃ | H | OCH₃ | H | 145.6 |
| 9 | aniline | H | H | H | H | H | H | 115-116 |
| 10 | 3',4'-dimethylaniline | H | H | CH₃ | CH₃ | H | H | 114-116 |

EXAMPLE 2

Examination of Cell Survival (MTT Assay)

In this example, 3-(4,5-dimethylthiazol-2-yl)-2,5-diphenyl tetrazolium bromide (MTT) was used to determine if the survival rate of BHK-21 cells, TE671cells and RD cells would be influenced when being treated with different concentrations of compound 1 prepared in Example 1. The concentration of 50% cytotoxicity (CC50) of compound 1 in BHK-21 cells, TE671cells and RD cells was also calculated.

MTT is a water-soluble tetrazolium salt which can react in the mitochondrial respiratory chain in living cells to metabolize and reduce the tetrazolium bromide shown in the structure of MTT and to form an water-insoluble purple crystal formazan under the reaction of succinate dehydrogenase (SDH) and cytochrome c (cyt c). The amount of the produced crystal is directly proportional to the number of living cells (because the SDH will disappear from dead cells, and thus, the MTT cannot be reduced). Furthermore, a mitochondrium is an organelle in cells that is most sensitive to the environment, and thus, the MTT assay can serve as a marker for the survival rate of cells treated by the drug.

BHK-21 cells, TE671cells and RD cells were cultured in a 96-well culture plate, respectively, with an initial density of 3×10³ per well, and with 100 µl of 2% FBS-containing MEM medium per well. The culture plate was placed into an incubator (37° C., 5% CO₂) and incubated overnight. Then, the medium was removed after the cells adhered to the plate. Fresh medium and compound 1 were added into each well of the culture plate, wherein the final concentration of compound 1 was about 0, 2.5, 25, 125, 250 and 500 µM, respectively. The culture plate was placed into an incubator (37° C., 5% CO₂) and incubated for 48 hours. The medium was removed and 10 µl of MTT reagent 1 was added into each well of the culture plate and maintained in the dark for 4 hours. The medium was then removed. MTT reagent 2 (100 µl) was added into each well of the culture plate and maintained in the dark for 1 hour. The absorbances of the samples were measured by ELISA at a wavelength of 570/630 nm. The results are shown in FIGS. 1A to 1C.

Figure 1B:
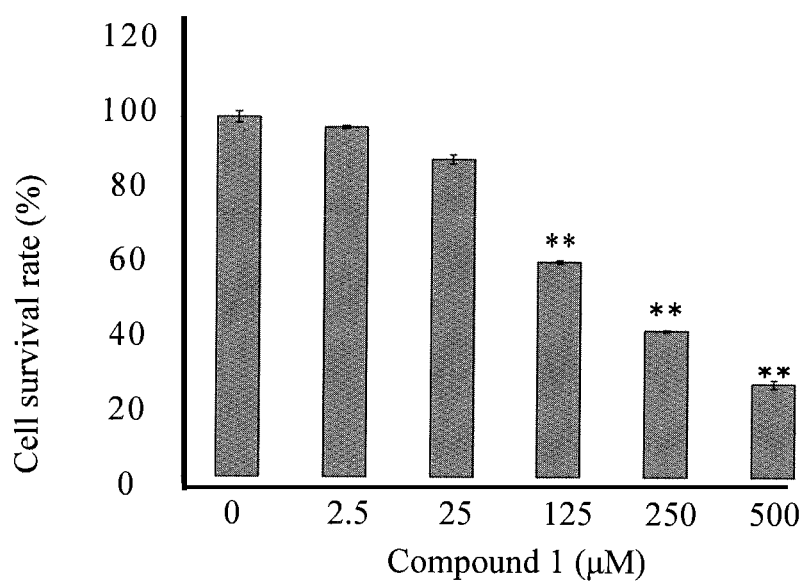
Figure 1C:
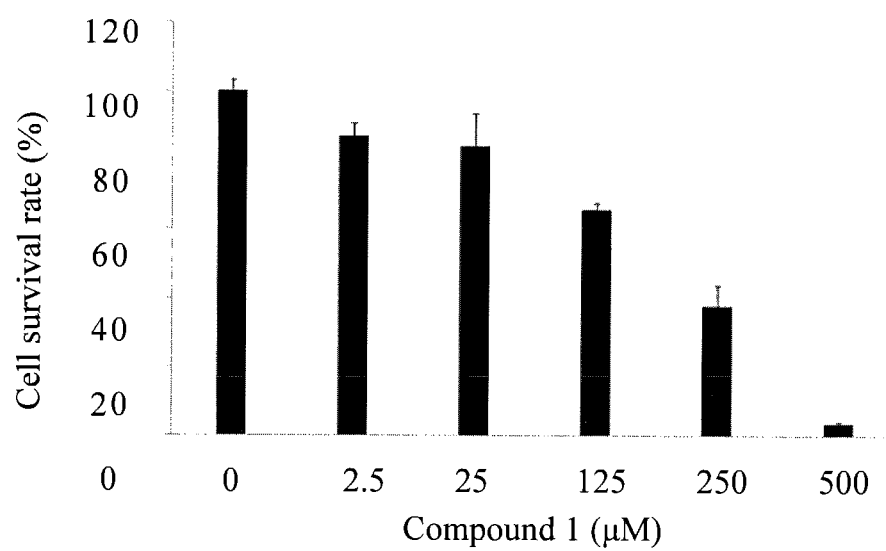

As shown in FIGS. 1A to 1C, the concentration of 50% cytotoxicity of compound 1 in BHK-21 cells is greater than 500 µM. In addition, the concentration of 50% cytotoxicity of compound 1 in TE671 cells and RD cells are 189 µM and 222 µM, respectively. These results show that the cytotoxicity of compound 1 in BHK-21 cells, TE671cells and RD cells are very low. Compound 1 will not affect the cell survival rate of the cells.

EXAMPLE 3

Inhibition of Japanese Encephalitis Virus Infection-Induced Cytopathic Effect and Apoptosis (1) BHK-21 Cells and TE671cells were Infected with JEV T1P1

BHK-21 cells and/or TE671cells were separately cultured in a 24-well culture plate, with an initial density of 3×10⁴ per well, and with 1 ml of 2% FBS-containing MEM medium per well. The cells were incubated in an incubator (37° C., 5% CO₂) overnight, and the medium was removed until the cells adhered to the plate. Then, fresh 2% FBS-containing MEM medium was simultaneously added into each well of the culture plate. The cells were infected with a JEV T1P1 virus strain, wherein the amount of JEV T1P1 used to infect BHK-21 cells was a multiplicity of infection (M.O.I.)=0.1, and the amount of JEV T1P1 used to infect TE671 cells was M.O.I.=0.05. Different concentrations of compound 1 (final concentrations were 0, 2.5, 25 and 125 µM, respectively) were added into different wells. The culture plate was placed into an incubator (37° C., 5% CO₂) and maintained therein.

(2) Cytopathic Effect Test

Figure 2A:
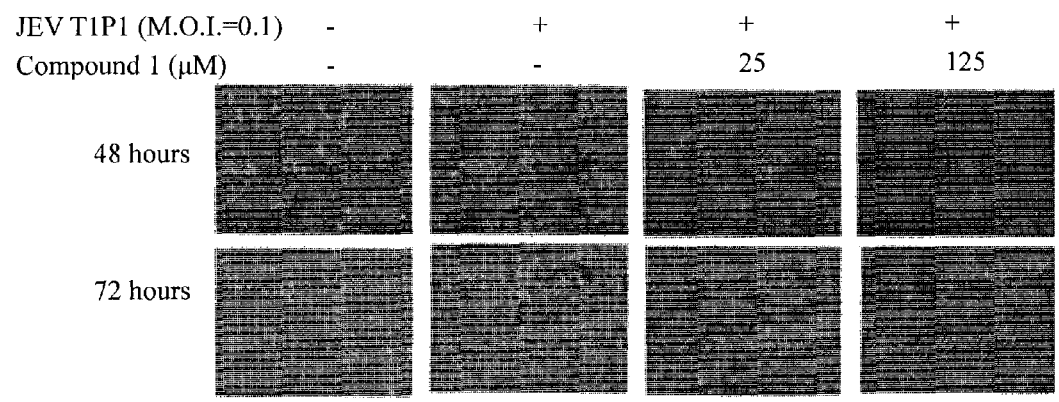
FIGS. 2A and 2B are photographs showing that compound (1) inhibits JEV T1P1 infection-induced cytopathic effect of BHK-21 cells (FIG. 2A) and TE671 cells (FIG. 2B), respectively.
Figure 2B:
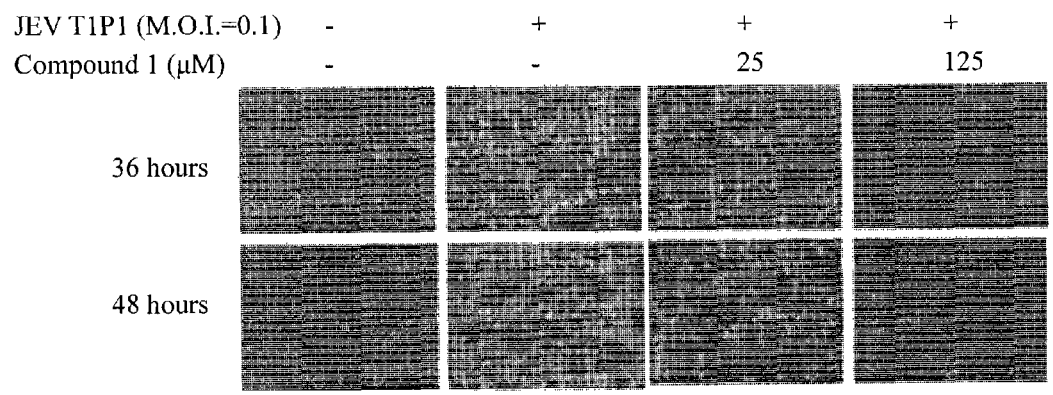

When BHK-21 cells were infected with JEV T1P1 virus strain for 48 and 72 hours as indicated in the above experiment (1), the cytopathic effect was observed by photography, while the cytopathic effect of TE671 cells was observed by photography when TE671 cells were infected with the JEV T1P1 virus strain for 36 and 48 hours. The results are shown in FIGS. 2A and 2B. In addition, 200 μl culture medium supernatant of both cells was collected from each time point (i.e., 48 and 72 hours), thereby, providing the use for a viral plaque test in Example 4.

As known by the morphology of BHK-21 cells that is observed in FIG. 2A, BHK-21 cells have shown an obvious cytopathic effect when infected with JEV T1P1 for 48 hours. This cytopathic effect would be significantly reduced when treating with compound 1 (25 μM) simultaneously. Furthermore, BHK-21 cells have shown a serious cytopathic effect (or even have died) when the infection time was prolonged to 72 hours, while this cytopathic effect would be still effectively inhibited when treating with compound 1 (125 μM) simultaneously.

As known by the morphology of TE671 cells observed in FIG. 2B, TE671 cells have shown an obvious cytopathic effect when infected with JEV T1P1 for 36 hours, while the cytopathic effect would be inhibited when treating with compound 1 (25 μM) simultaneously. Furthermore, the cytopathic effect could be still inhibited when the cells were treated with compound 1 (25 μM), even if the time for TE671 cells infected with JEV T1P1 virus strain was prolonged to 48 hours.

(3) Apoptosis Test

BHK-21 cells and TE 671 cells were washed with PBS after being infected with the JEV T1P1 virus strain for 36 hours in the above experiment (1). Then, PBS was removed. Trypsin-EDTA (150 μl) was added into each well. The cells were incubated in an incubator at 37° C. for 3 minutes. Then, 1 ml MEM medium was added into each well to neutralize EDTA. The cells were collected in a 15 ml tube and precipitated by centrifugation (2000 rpm, 3 minutes). The supernatant was removed and the cells were resuspended with 1 ml PBS per tube and then precipitated by centrifugation (2000 rpm, 3 minutes). The supernatant was removed and the cells in different tubes were transferred into various FACS tubes and stained. For the unstained group, only 500 μl of binding buffer was added. For the Annexin V-single stained group, 10 Annexin V and 490 μl binding buffer were added. For the PI-single stained group, 10 μl PI and 490 μl binding buffer were added. The cells were maintained in the dark for 5 to 10 minutes, and then analyzed by flow cytomerty. The results are shown in FIGS. 3A, 3B, 4A and 4B.

Figure 3A:
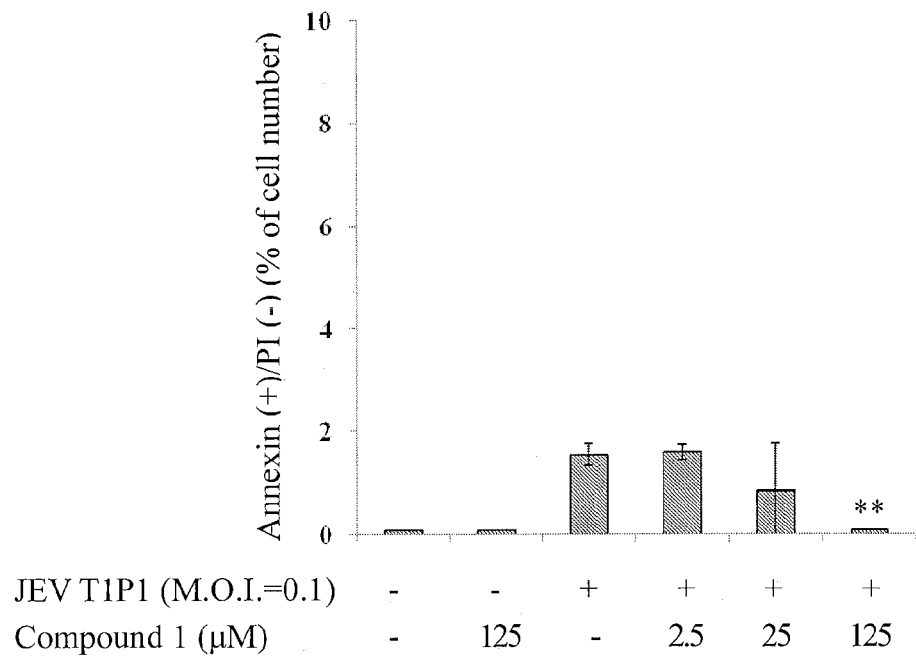
FIGS. 3A and 3B are statistical bar diagrams showing the ratio of BHK-21 cells that get into early apoptosis (FIG. 3A) and late apoptosis (FIG. 3B) (*$p<0.005$: represents a statistical significance; **$p<0.001$: represents a statistical significance), wherein the vertical axis represents the percentage of cell numbers, the upper row of the horizontal axis represents there is a JEV T1P1 infection (+) or not (−); and the lower row of the horizontal axis represents the concentration of compound (1)
Figure 3B:
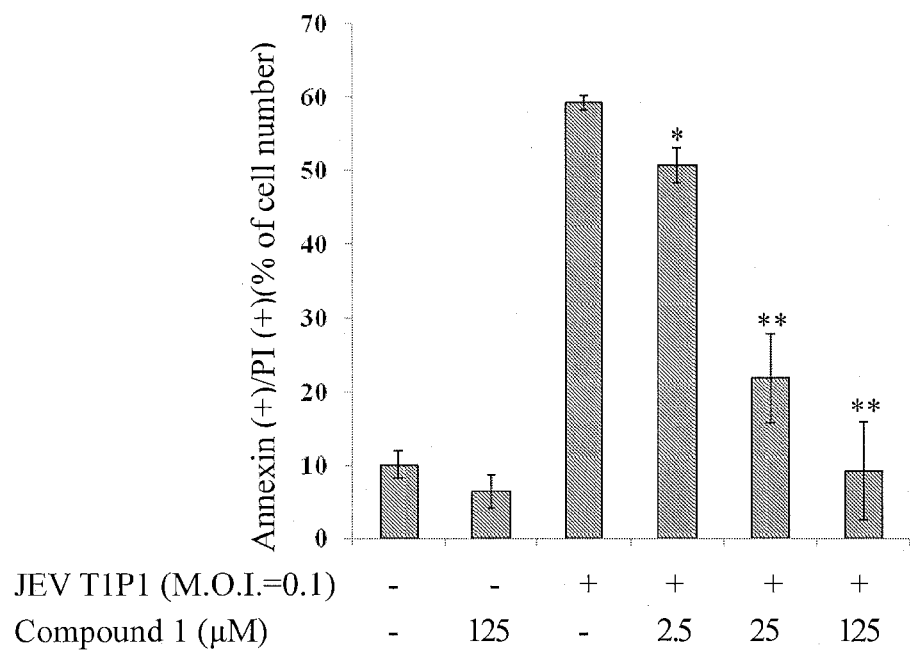

As shown in FIGS. 3A and 3B, 59.05% BHK-21 cells were getting into late apoptosis after being infected with JEV T1P1 for 36 hours. The ratio of BHK-21 cells getting intolate apoptosis was reduced by compound 1 in a concentration dependent manner. The result shows that compound 1 has an ability of inhibiting Japan encephalitis virus-induced cytopathic effect of BHK-21 cells.

Figure 4A:
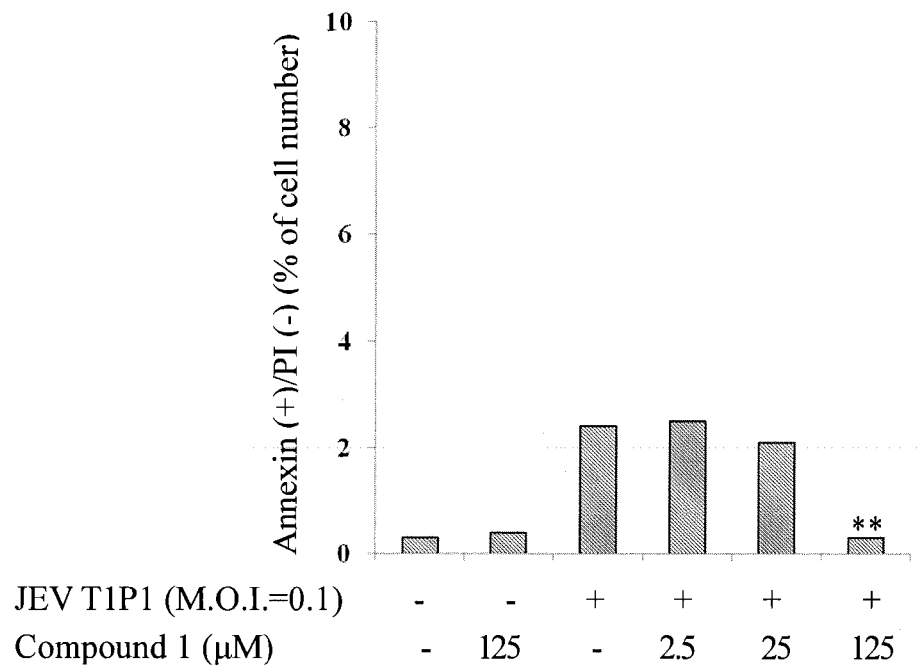
FIGS. 4A and 4B are statistical bar diagrams showing the ratio of TE671 cells that get into early apoptosis (FIG. 4A) and late apoptosis (FIG. 4B) (*$p<0.005$: represents a statistical significance; **$p<0.001$: represents a statistical significance), wherein the vertical axis represents the percentage of cell numbers, the upper row of the horizontal axis represents there is a JEV T1P1 infection (+) or not (−); and the lower row of the horizontal axis represents the concentration of compound (1)
Figure 4B:
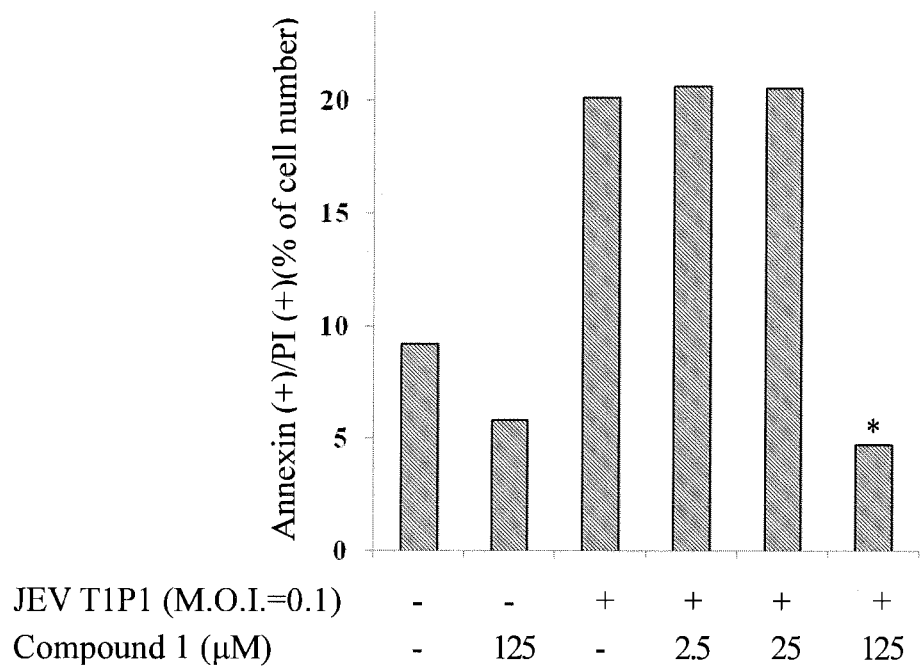

Furthermore, as shown in FIGS. 4A and 4B, 20.1% TE671 cells were getting into late apoptosis after being infected with JEV T1P1 for 36 hours, while the ratio of TE671 cells getting into late apoptosis was reduced to 4.7% by treating with 125 μM of compound 1. The results show that compound 1 has an ability of inhibiting the Japan encephalitis virus-induced cytopathic effect of TE671 cells.

EXAMPLE 4

Inhibition of Japan Encephalitis Virus Replication (Viral Plaque Test)

BHK-21 cells were cultured in a 6-well culture plate at an initial density of $3 \times 10^5$ per well with 2 ml of 2% FBS-containing MEM medium per well. The cells were incubated in an incubator (37° C., 5% $CO_2$) overnight, and the medium was removed until the cells adhered to the plate. Then, 200 μl of $10^4$ times diluted-supernant (48 and 72 hours) collected in the above experiment (2) of Example 3 was added into each well. The cells were incubated in an incubator (37° C., 5% $CO_2$) and the culture plate was patted gently every 15 minutes to cover all the cells with the supernatant. The medium was removed after incubating for 1 hour. A fresh 2% FBS-containing MEM medium (3 ml) was added into each well and the cells were incubated for 3 days. The medium was removed. Naphthol Blue Black dye was added into each well and the cells were stained at room temperature overnight. The cells were washed with clear water, and then the viral plaques were counted to calculate the virus titer. The results are shown in FIGS. 5A, 5B, 6A and 6B.

Figure 5A:
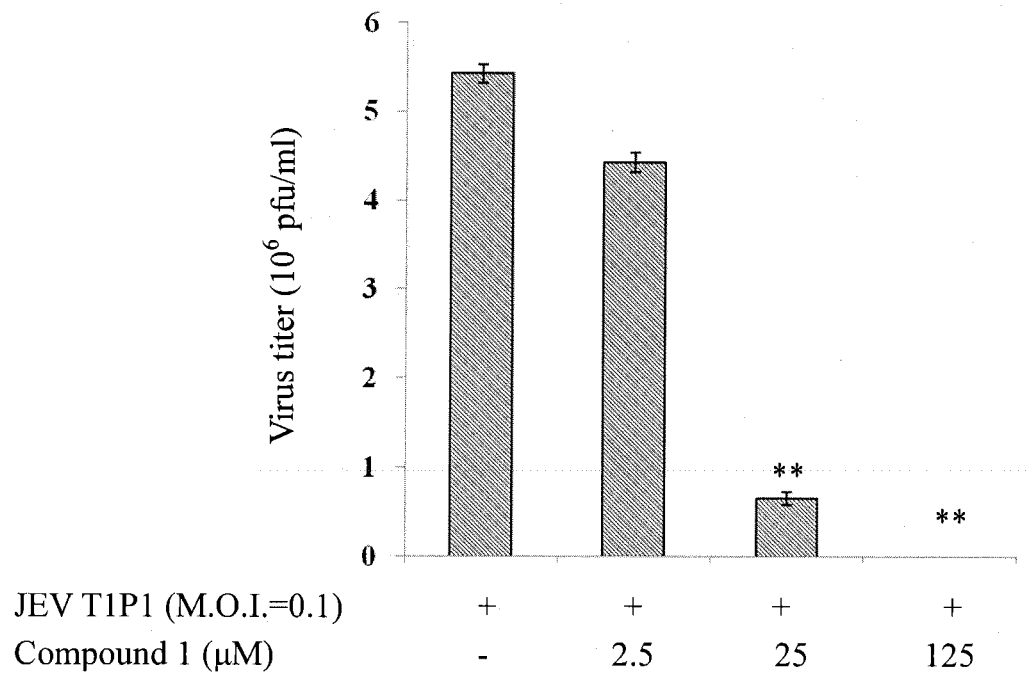
FIGS. 5A and 5B are statistical bar diagrams showing the replication of JEV T1P1 in BHK-21 cells which have been infected with JEV T1P1 for 48 hours (FIG. 5A) or 72 hours (FIG. 5B) (*p<0.005: represents a statistical significance; **p<0.001: represents a statistical significance), wherein the vertical axis represents a virus titer, the upper row of the horizontal axis represents there is a JEV T1P1 infection (+); and the lower row of the horizontal axis represents the concentration of compound (1)
Figure 5B:
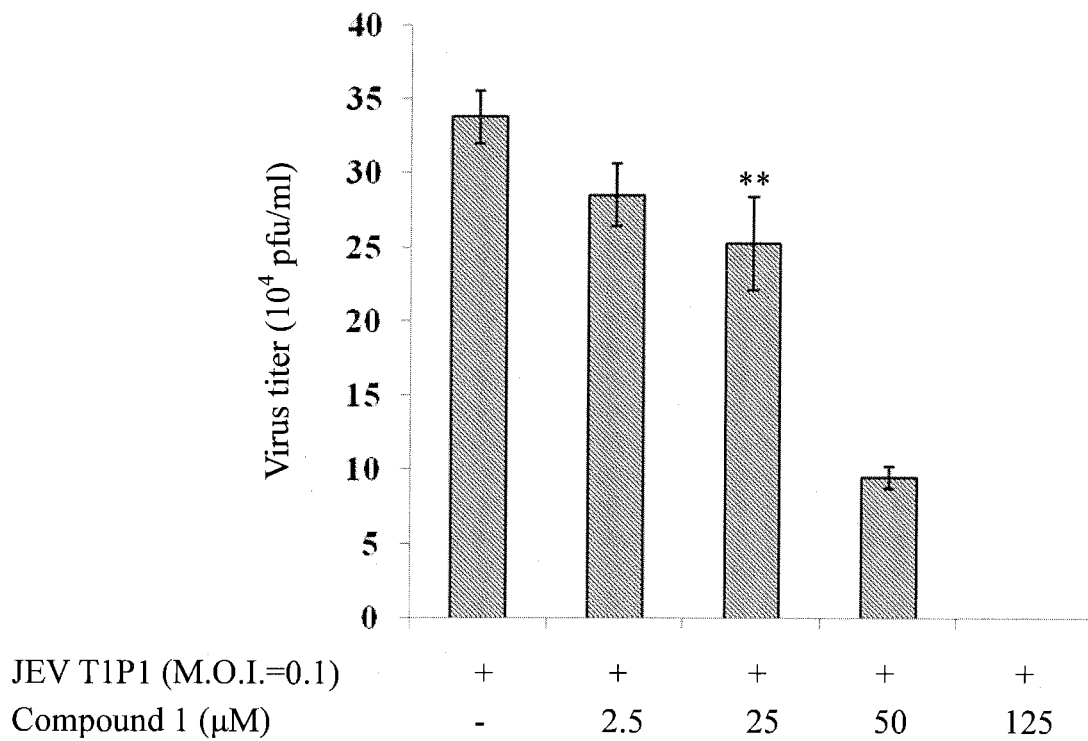
Figures 6A, 6B:
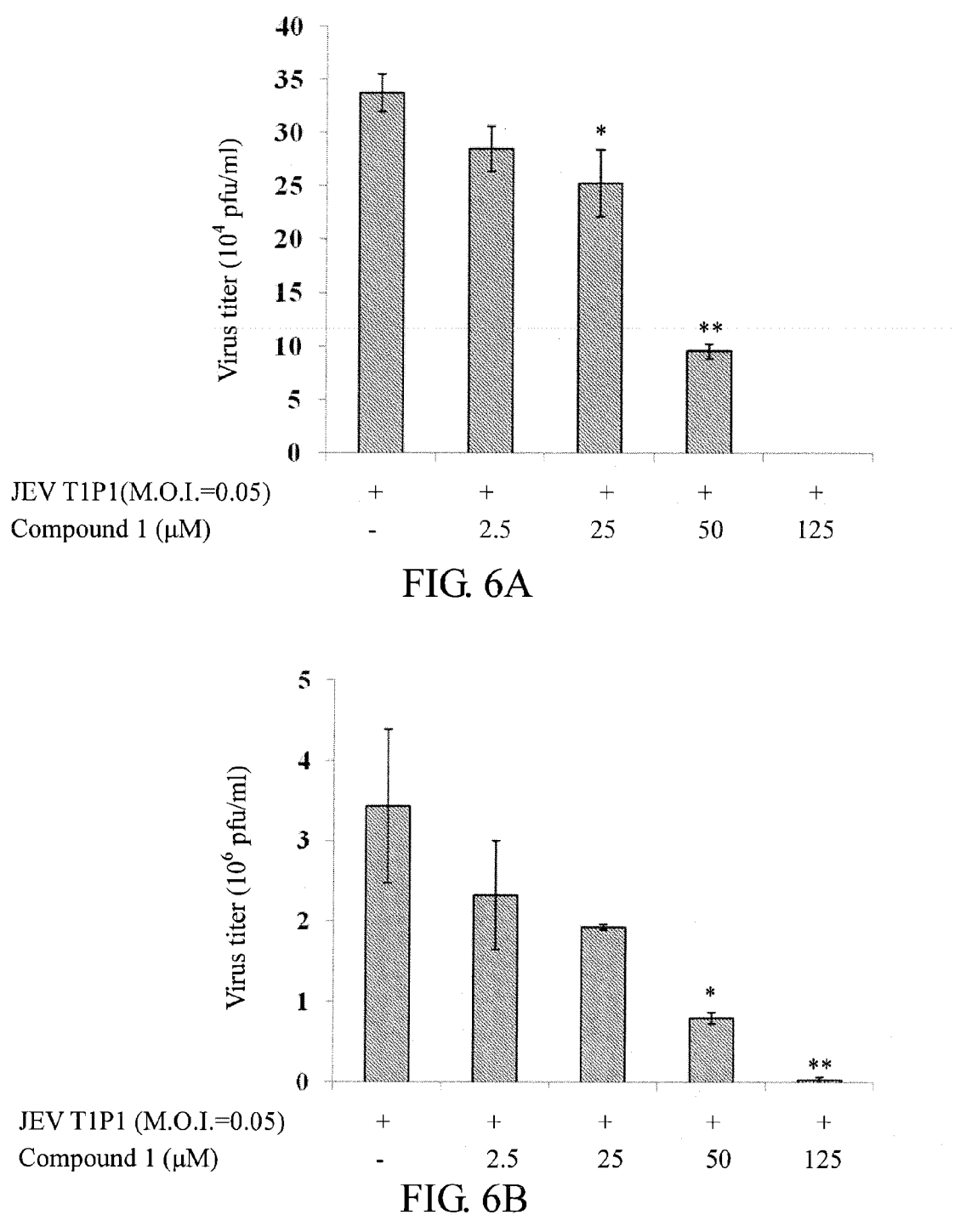

As shown in FIGS. 5A and 5B, the replication of JEV T1P1 in BHK-21 cells was significantly decreased after the JEV T1P1 infected-BHK-21 cells were treated with compound 1 for 48 or 72 hours. Furthermore, as the results shown in FIGS. 6A and 6B, the replication of JEV T1P1 in TE671 cells was significantly decreased after the JEV T1P1 infected-TE671 cells were treated with compound 1 for 36 or 48 hours. The aforesaid results show that compound 1 has an ability of inhibiting Japan encephalitis virus replication.

EXAMPLE 5

Analysis of the Mechanisms of Anti-Virus

TE671cells were cultured in a 6-well culture plate at an initial density of $3 \times 10^5$ per well with 2 ml of 2% FBS-containing MEM medium per well. The cells were incubated in an incubator (37° C., 5% $CO_2$) overnight. The medium was removed until the cells adhered to the plate. 1 ml of fresh 2% FBS-containing MEM medium was simultaneously added into each well. The cells were infected with JEV T1P1virus strain (M.O.I.=0.05). Different concentrations of compound 1 (the final concentrations were 0, 2.5, 25, 125 and 250 μM, respectively) were added into different wells. The cells were incubated in an incubator (37° C., 5% $CO_2$) for 36 hours. The supernatant was removed, and the TE671 cells were washed with PBS. The PBS was removed, and 150 μl Trypsin-EDTA was added into each well. The cells were incubated in an incubator at 37° C. for 3 minutes. Then, 1 ml MEM medium was added into each well to neutralize EDTA, and the cells were separately collected into 15 ml tubes and precipitated by centrifugation (2000 rpm, 3 minutes). The supernatants were removed. The cells were resuspended with 1 ml PBS per tube, transferred into 1.5 ml microtubes respectively, and precipitated by centrifugation (2000 rpm, 3 minutes). The supernatants were removed and 100 μl radioimmunoprecipitation buffer (RIPA buffer) was added into each well. The cells were placed at 4° C. for 15 to 30 minutes, and then ruptured by a sonicator (LEVEL3; ON/OFF: 2 seconds/2 seconds; time for rupturing: 10 seconds). The ruptured cells were then precipitated by centrifugation (2000 rpm, 3 minutes), and the protein supernatants were separately collected into fresh microtubes. A 2×SDS-PAGE sample loading buffer (100 μl) was added into each microtubes. The microtubes were heated in a 100° C. dry bath incubator for 5 minutes, placed on ice rapidly, and then stored at −20° C.

The above protein samples were analyzed by protein electrophoresis. First, the glass plates and gel assembly rack were fabricated. The separating gel prepared in accordance with the desired concentration of gel was poured thereinto, and then pressed flat by using 75% ethanol. Ethanol was poured off after the separating gel was polymerized. The previously prepared 4% stacking gel was poured thereinto. Then, a sample well comb was inserted. The sample well comb was removed after the stacking gel was polymerized. The gel rack was placed in an electrophoresis device. A 1× running buffer was poured into the electrophoresis device. A marker (3.5 µl) was loaded into a well, and 10 µl of each protein sample was loaded into other wells. The electrophoresis was started (voltage: 60 volt (V); time: 30 minutes). The voltage was turned to 120 V until the blue dye entered the separating gel and the marker was separated. The electrophoresis continued for 1.5 hours. The stacking gel was cut out until the blue dye moved to the bottom of gel. Then, protein transfer was conducted.

The previously prepared foam rubbers, nitrocellulose membranes, 3M filter paper and the above electrophoresis gel were immersed in a transfer buffer. Then, one foam rubber, two 3M filter papers, one nitrocellulose membrane, electrophoresis gel, two 3M filter papers, and one foam rubber were placed sequentially from the positive to negative pole. The bubbles between each layer were removed carefully by pressing. The electric plate was closed and put into a wet transfer tank (Bio-Rad) to conduct protein transfer (4° C., 90 V, 400 mA, 90 minutes). Finally, a western blotting was conducted after the proteins were transferred to the nitrocellulose membrane. The nitrocellulose membrane was immersed in a 1% BSA-containing block buffer, and shaken at room temperature for 1 to 1.5 hours. Then, a first antibody (diluted with 1% BSA to the concentration as recommended by the instruction of antibody) was added onto the membrane, and shaken for reaction at 4° C. overnight. The first antibody was retrieved. The membrane was washed with 1×TBST on a shaker 3 times for 20 minutes each time. Then, a secondary antibody was added onto the membrane, and shaken for reaction at room temperature for 2 hours. The membrane was washed with 1×TBST on a shaker 3 times for 20 minutes each time. A ECL coloring agent (reagent 1: reagent 2=1:1) was mixed and added onto the membrane. The membrane was put into a caseete immediately. The protein signal was presented by an X-ray film in a dark room. The results are shown in FIG. 7.

Figure 7:
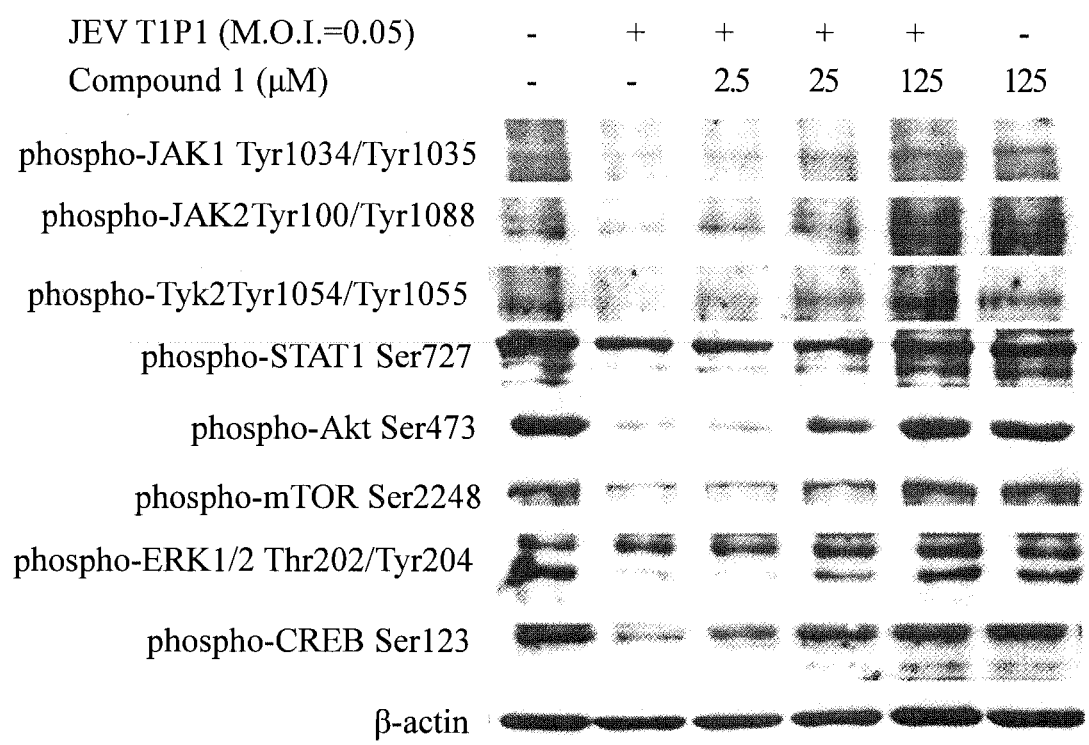
FIG. 7 is a western blot picture showing that compound (1) activates the JEV T1P1 infection-suppressed phosphorylation of Janus kinase-signal transducer and activator of transcription (JAK-STAT) signaling pathway-related proteins, protein kinase AkT-mammalian target of rapamycin (AkT-mTOR) signaling pathway-related proteins, and extracellular signal-regulated kinase-cAMP response element-binding protein (ERK-CREB) signaling pathway-related proteins (JAK1 represents Janus kinase 1; JAK2 represents Janus kinase 2; Tyk2 represents tyrosine kinase 2; STAT1 represents signal transducer and activator of transcription 1; mTOR represents mammalian target of rapamycin; ERK1/2 represents extracellular signal-regulated kinase 1/2; CREB represents cAMP response element-binding protein; Tyr represents tyrosine; Ser represents serine; Thr represents threonine)
Figure 8A:
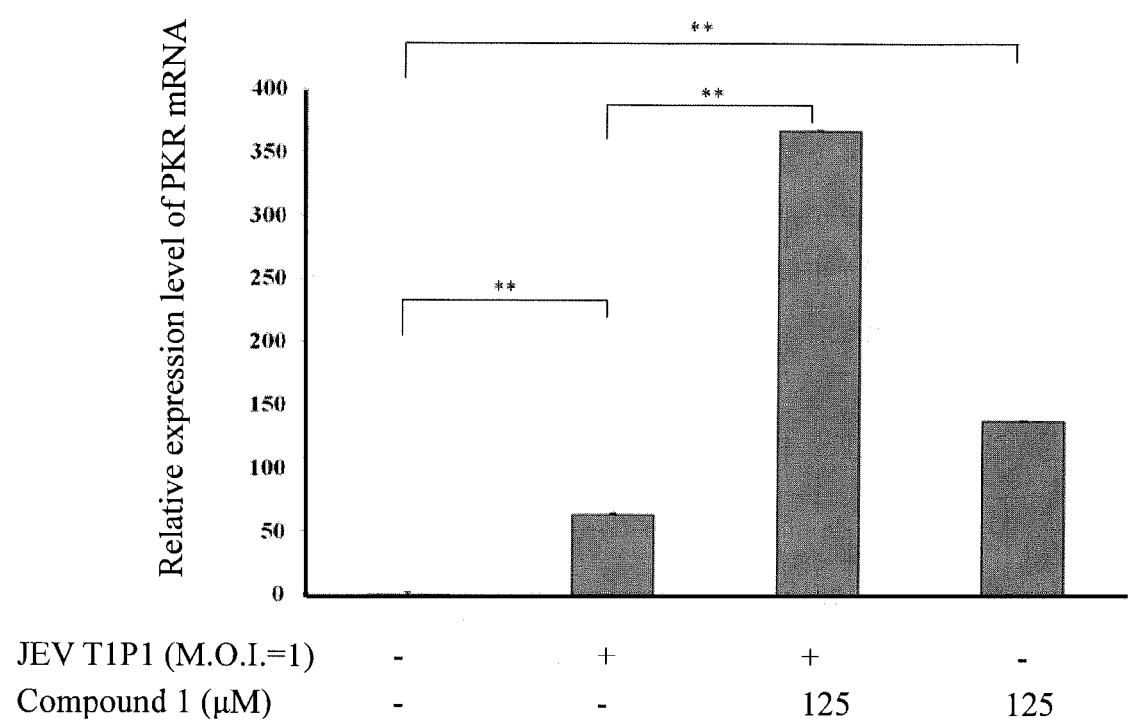
FIGS. 8A to 8E are statistical bar diagrams showing that compound (1) activates the relative expression levels of anti-virus genes in TE671 cells (*p<0.005: represents a statistical significance; **p<0.001: represents a statistical significance), wherein the vertical axis represents the relative expression levels of anti-virus genes, the upper row of the horizontal axis represents there is a JEV T1P1 infection (+) or not (−); and the lower row of the horizontal axis represents the concentration of compound (1)
Figure 8B:
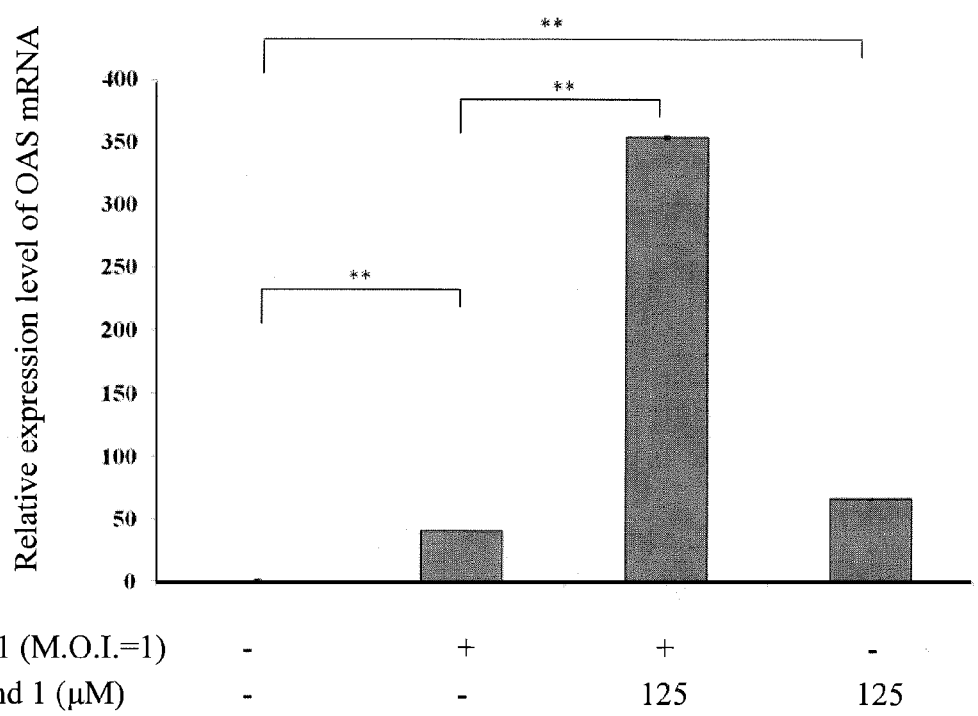
Figure 8C:
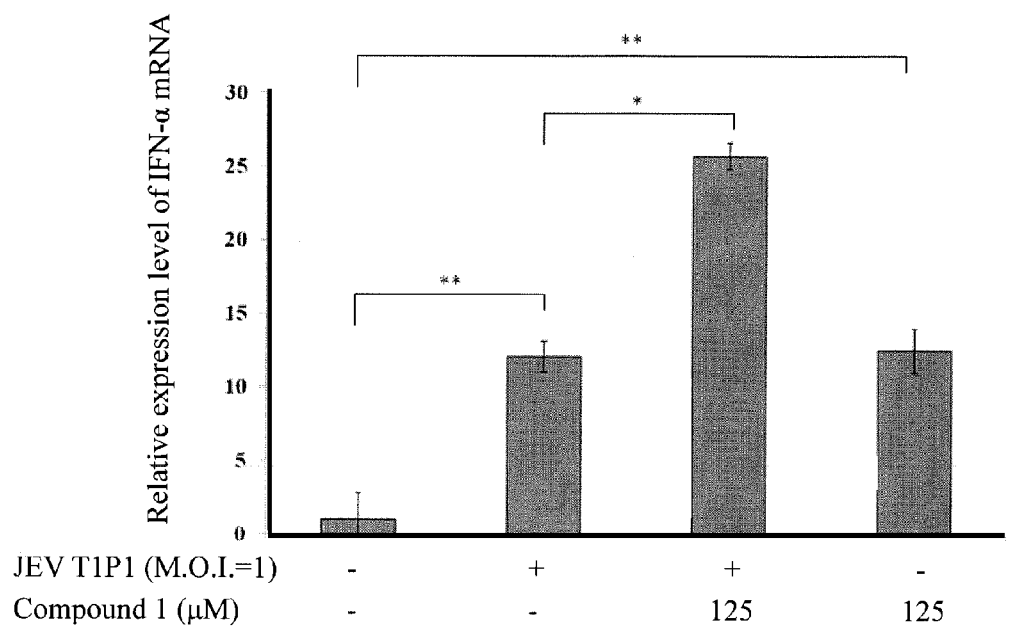
Figure 8D:
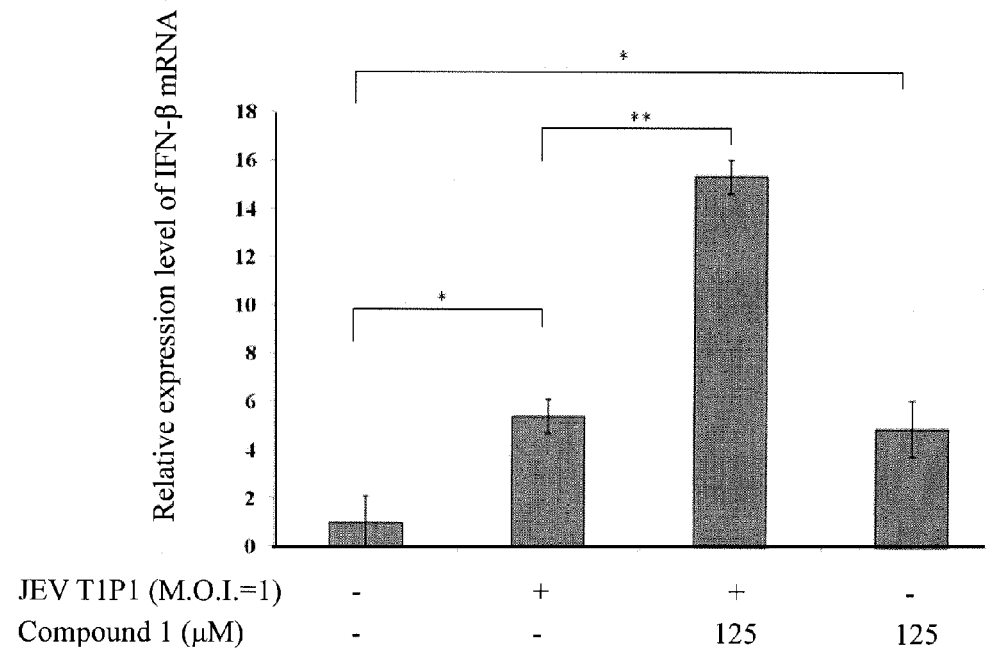
Figure 8E:
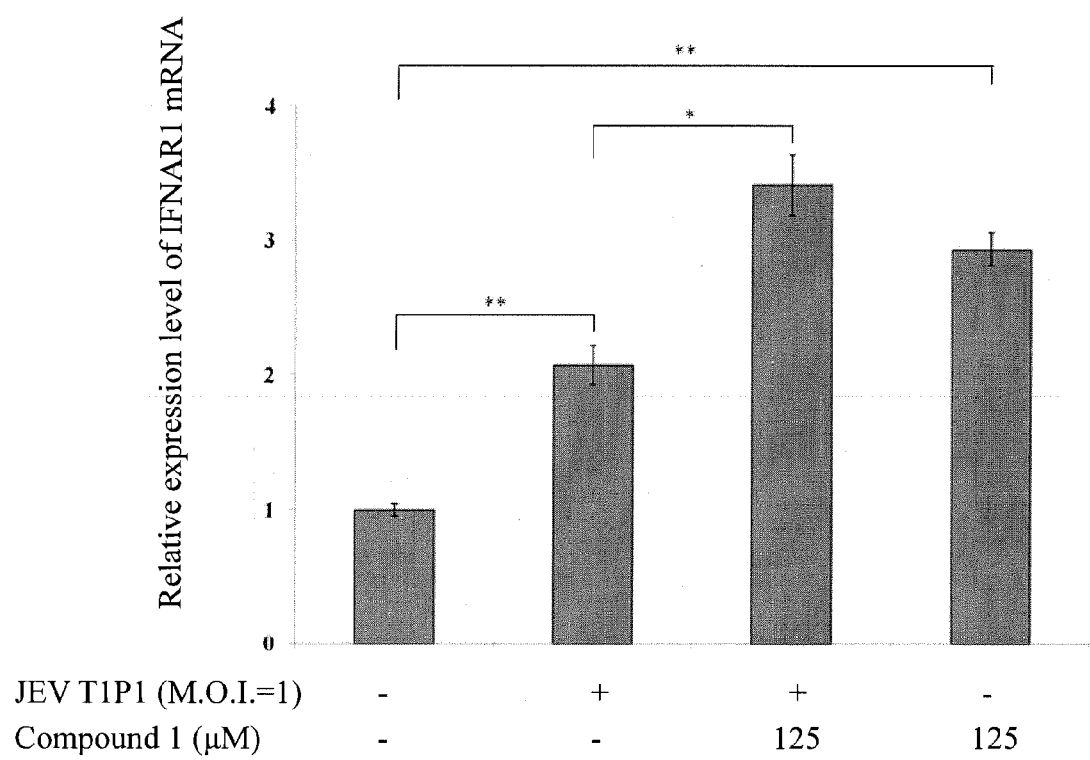

As shown in FIG. 7, after TE671 cells were infected with JEV T1P1, the phosphorylation levels of JAK-STAT signaling pathway-related proteins, AkT-mTOR signaling pathway-related proteins, and ERK-CREB signaling pathway-related proteins in TE671 cells were significantly decreased. The phosphorylation levels of the JEV T1P1 infection induced-signaling pathways were increased in a concentration dependent manner by a simultaneous treatment of compound 1. This result shows that compound 1 has an ability of activating the mechanisms of anti-virus.

EXAMPLE 6

Analysis of the Expression of Anti-Virus Genes

TE671 cells were cultured in a 6-well culture plate in accordance with the experimental conditions. The next day, TE671 cells were infected with the JEV T1P1 virus strain (M.O.I.=1), and various concentrations (the final concentration of compound 1 were about 0 or 125 respectively) of compound 1 were added into different wells simultaneously. The cells were then incubated in an incubator (37° C., 5% $CO_2$) for 8 hours, and then collected. The cells were re-suspended with PBS and precipitated by centrifugation (2000 rpm, 5 minutes), and then extracted by Pure Link RNA Mini Kit to obtain the RNA. If the obtained RNA was desired to be stored at −20° C., then the RNA would have to reverse transcribed into cDNA using the following reverse transcription PCR (RT-PCR) steps: i) 11 µl RNA was placed into a microtube, and put into a 55° C. PCR machine, and maintained for 15 minutes; ii) 1 µl dNTP and Oligo dT were added, and maintained at 65° C. for 10 minutes; iii) 2 µl DTT and 4 µl 5× First stand buffer were added, and maintained at 42° C. for 1 minute; iv) 1 µl Superscript IV Transcriptase was added, and maintained at 42° C. for 62 minutes; v) maintained at 72° C. for 15 minutes to stop the reaction (i.e., lead Superscript IV Transcriptase to lose activity). The cDNA obtained from the aforesaid steps can be stored at −20° C.

The expression of anti-virus genes was analyzed by real-time PCR. The cDNA mixture was separately added into 8-row microPCR tubes by an amount as follows: SYBR Green (12.5 nl), forward primer (1 µl), reverse primer (1 µl), $MgCl_2$ (1 µl), dd$H_2O$ (4.5 µl) and cDNA (5 µl). The aforesaid cDNA mixture was placed in a RT-PCR machine. The reaction conditions were set as follows: i) 95° C., 15 minutes; ii) 95° C. for 15 seconds and 60° C. for 1 minute. The conditions were kept for 40 cycles. Then, the amount of fluorescence of each cycle was determined by ABI Prism 7500 software. The fold difference of each gene as compared to the control group was calculated by using Ct to calculate $\Delta$Ct and $\Delta\Delta$Ct (i.e., $\Delta$Ct=Ct. exp−Ct. control, $\Delta\Delta$Ct=$\Delta$Ct. exp−$\Delta$Ct. mock). Then, $2^{-\Delta\Delta Ct}$ can thereby be calculated. The results are shown in FIGS. 8A to 8E.

As shown in FIGS. 8A to 8E, the treatment of compound 1 can increase the relative gene expression levels of PKR, OAS, IFN-α and interferon receptor in JEV T1P1-infected TE671 cells. The results show that compound 1 has an ability of promoting a virus-infected cell to express anti-virus genes.

EXAMPLE 7

Inhibition of Dengue Virus Infection-Induced Cytopathic Effect

BHK-21 cells were cultured in a 24-well culture plate at an initial density of $3\times10^4$ per well with 1 ml of 2% FBS-containing MEM medium per well. The cells were incubated in an incubator (37° C., 5% $CO_2$) overnight, and the medium was removed until the cells adhered to the plate. Then, 1 ml of fresh 2% FBS-containing MEM medium was simultaneously added into each well of the culture plate; the cells were infected with the DEN2 virus strain (M.O.I.=0.1); different concentrations of compound 1 (the final concentrations were 0, 2.5 and 25 µM, respectively) were added into different wells. BHK-21 cells were incubated in an incubator (37° C., 5% $CO_2$) for 72 hours, and then their morphology was observed by photography.

Figure 9:
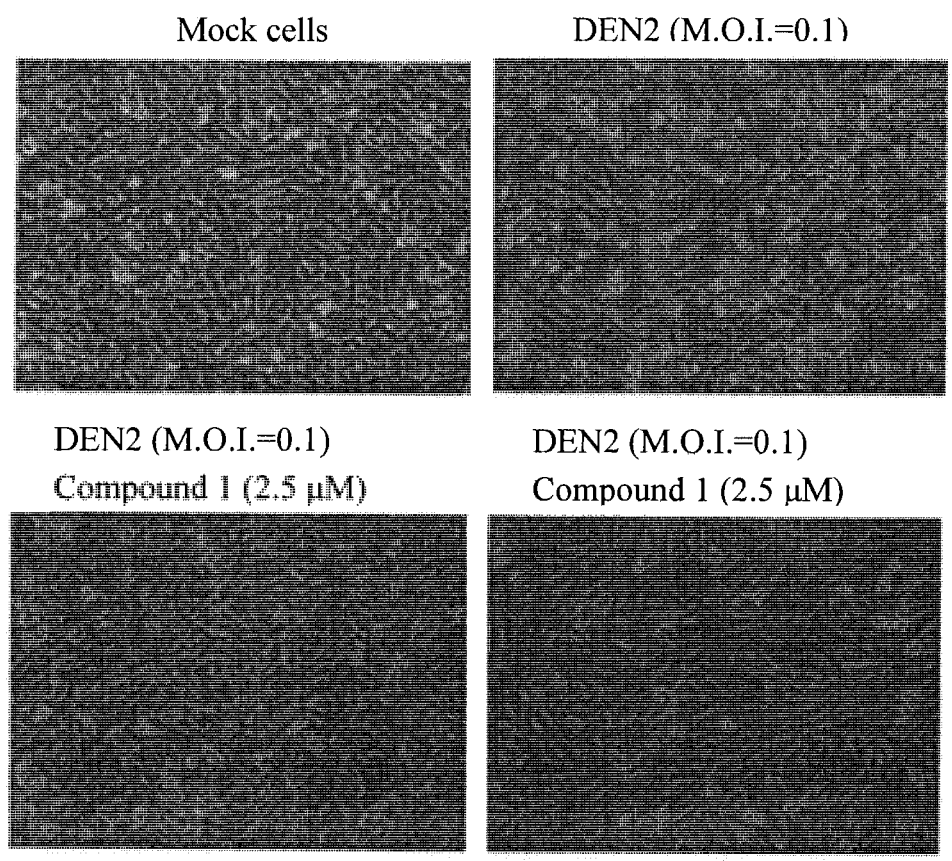
FIG. 9 is a photograph showing that compound (1) inhibits the DEN2 infection-induced cytopathic effect.

As shown in FIG. 9, there was a cytopathic effect in all BHK-21 cells infected with DEN2 for 72 hours. The cytopathic effect would be effectively inhibited by a simultaneous treatment of compound 1 (25 µM).

EXAMPLE 8

Inhibition of Dengue Virus Replication

Huh7 cells were cultured in a 24-well culture plate with an initial density of $3\times10^4$ per well, and with 1 ml of 2% FBS-containing MEM medium per well. The cells were incubated in an incubator (37° C., 5% $CO_2$) overnight. The medium was removed until the cells adhered to the plate. Then, 1 ml of fresh 2% FBS-containing MEM medium was simultaneously added into each well of the culture plate. The cells were infected with DEN2 virus strain (M.O.I.=5). Different concentrations of compound 1 (the final concentrations were 0, 10, 50, 100 and 150 μM, respectively) were added into different wells. The culture plate was placed into an incubator (37° C., 5% $CO_2$) and maintained for 48 hours. The supernatant of viral medium was collected.

The above obtained supernatant was analyzed by an antigen-capture enzyme-linked immunosorbent assay (ELASA) to quantitate the DEN2 NSI protein level in the viral medium. First, a NS1 antibody was added into each well of a 96-well micro-reaction plate (200 μl/well) and the reaction was maintained at 4° C. overnight. Each well was washed with PBST 3 times (200 μl/time). A 1% BSA-containing blocking buffer (300 μl) was added into each well. The reaction was maintained at room temperature for 1 hour, and then the blocking buffer was removed. Recombinant NS1 protein (rNS1) serially diluted and 200 μl of supernatant denatured at 95° C. for 3 minutes were added into each well. The reaction was maintained at room temperature for 1 hour. All liquid was removed. An anti-NS1 rabbit polyclonal antibody with biotin was added into each well, and the reaction was maintained at room temperature for 1 hour. Each well was washed with 200 μl of PBST for 3 times. Strepavidin-HRP was added into each well (200 μl/well). The reaction was maintained at room temperature for 20 minutes. Each well was washed with PBST 3 times (200 μl/time). Finally, TMB (200 μl/well) was added and maintained at room temperature for 10 minutes for color reaction. $H_2SO_4$ (2N, 100 μl/well) was added to stop the reaction. The reading value of DEN NS1 protein amount in each supernatant was determined by examining the absorbances at a wavelength of 450 nm to evaluate DEN2 replication. The result is shown in FIG. 10.

Figure 10:
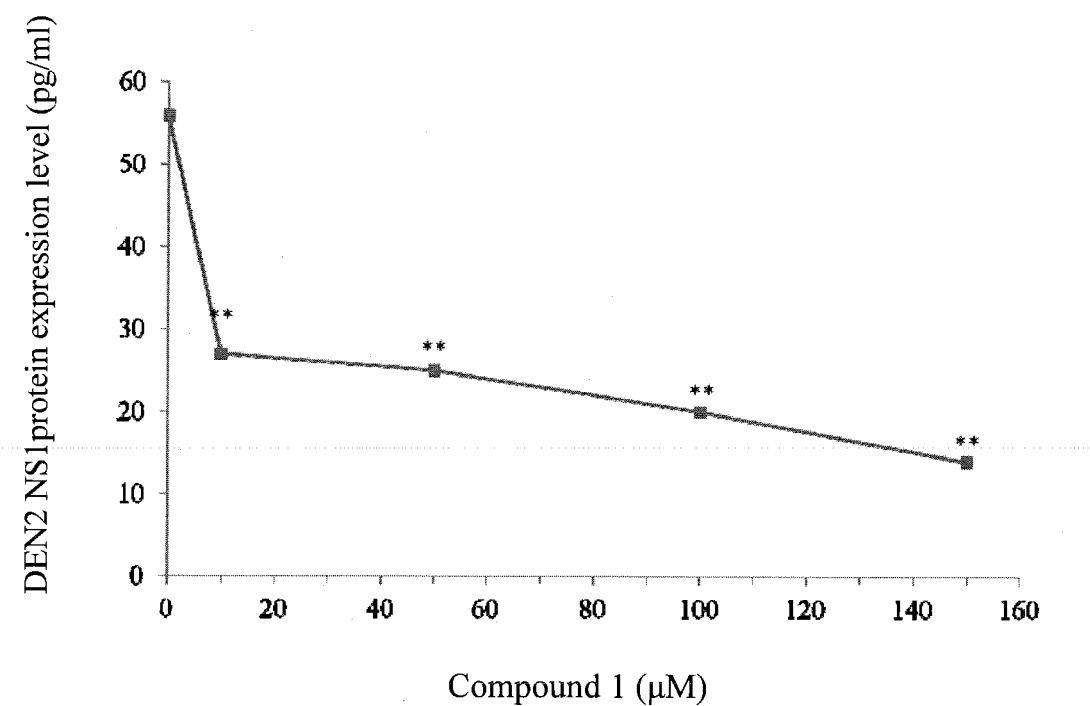
FIG. 10 is a curve diagram showing that compound (1) inhibits the DEN2 replication in Hyh7 cells, wherein the vertical axis represents the expression level of DEN2 NS1 protein and the horizontal axis represents the concentration of compound (1)
Figure 11:
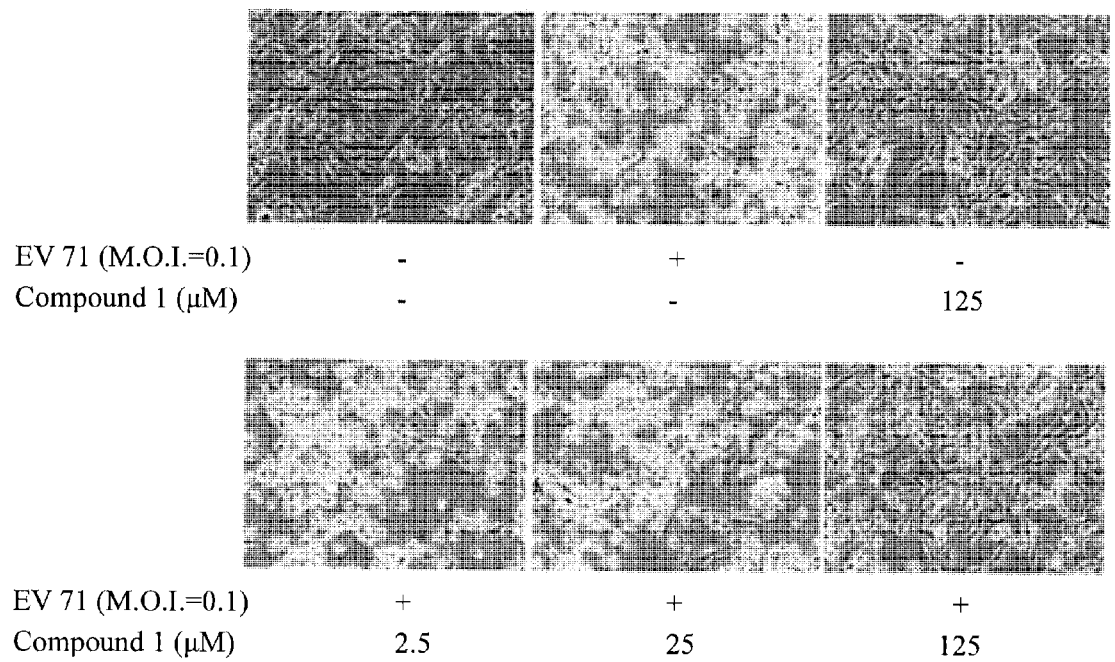
FIG. 11 is a photograph showing that the compound (1) inhibits an *enterovirus* infection-induced cytopathic effect.

As shown in FIG. 10, the level of DEN2 NS1 protein is reduced by treating with 10 μM of compound 1. This result shows that compound 1 can effectively reduce the dengue virus replication in a virus-infected cell.

EXAMPLE 9

Inhibition of *Enterovirus* Infection-Induced Cytopathic Effect

RD cells were cultured in a 24-well culture plate at an initial density of $3\times10^4$ per well with 1 ml of 2% FBS-containing MEM medium per well. The cells were incubated in an incubator (37° C., 5% $CO_2$) overnight. The medium was removed, and then 1 ml of fresh 2% FBS-containing MEM medium was simultaneously added into each well. The RD cells were infected with EV71 virus strain (M.O.I.=0.1). Different concentrations of compound 1 (final concentrations were 0, 2.5, 25 and 125 μM) were added into different wells. The RD cells were incubated in an incubator (37° C., 5% $CO_2$) for 36 hours, and then their morphology was observed by photography.

As shown in FIG. 10, there was a cytopathic effect in all RD cells infected with EV71 for 36 hours. The cytopathic effect would be effectively inhibited by a simultaneous treatment with compound 1 (125 μM).

EXAMPLE 10

Inhibition of *Enterovirus* Replication

The RD cells were cultured in a 24-well culture plate with an initial density of $3\times10^4$ per well, as well as with 1 ml of 2% FBS-containing MEM medium per well. The cells were incubated in an incubator (37° C., 5% $CO_2$) overnight. The medium was removed, and then, 1 ml of fresh 2% FBS-containing MEM medium was simultaneously added into each well. The RD cells were infected with an EV71 virus strain (M.O.I.=0.1). Different concentrations of compound 1 (final concentrations were 0, 2.5, 25 and 125 μM) were added into different wells respectively. RD cells were incubated in an incubator (37° C., 5% $CO_2$) for 36 hours, and then the viral medium was collected for the following plaque test.

The RD cells were cultured in a 6-well culture plate, and incubated in an incubator (37° C., 5% $CO_2$) overnight. The medium was removed, and then 200 μl of the above $10^4$ times diluted viral medium was added into each well. The cells were infected for 1 hour. Then, 3 ml of a 3% agarose covering solution was added into each well. The cells were incubated in an incubator (37° C., 5% $CO_2$) for 3 days. The covering solution was removed. Methyl blue was added into each well, and the plate was placed at room temperature overnight, and then washed with clear water, and dried. The number of plaques was counted to calculate the virus titer and inhibitory rate. The results are shown in FIGS. 12A and 12B.

Figure 12A:
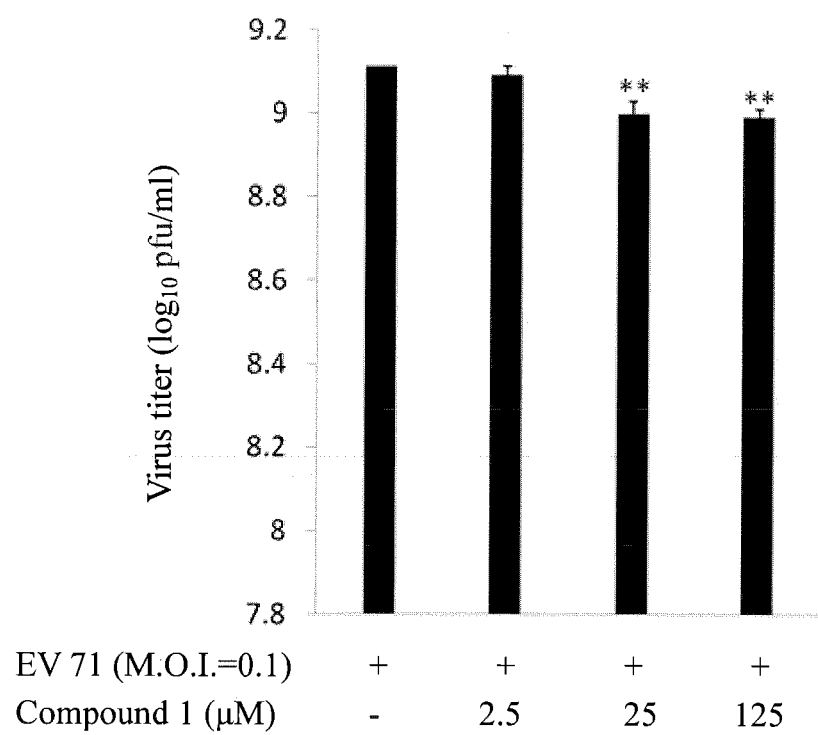
FIGS. 12A and 12B are statistical bar diagrams showing the *enterovirus* replication in RD cells treated by compound (1) (**p<0.001: represents a statistical significance), wherein the vertical axis represents the percentage of inhibition, the upper row of the horizontal axis represents there is a EV71 infection (+); and the lower row of the horizontal axis represents the concentration of compound (1)
Figure 12B:
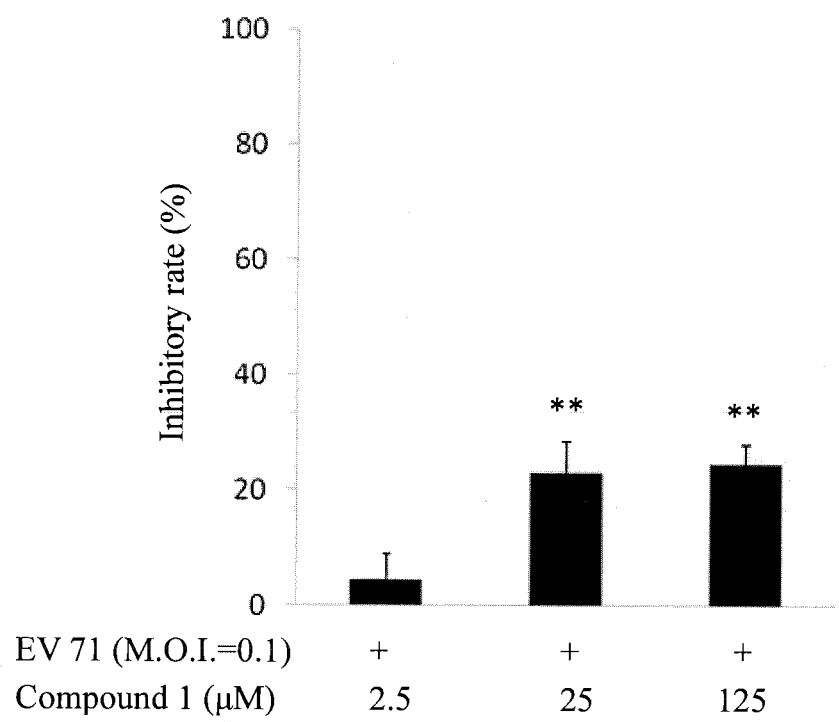

As shown in FIGS. 12A and 12B, the inhibitory rates of EV 71 replication in RD cells treated with compound 1 at 2.5, 25 and 125 μM were 4.6%, 23% and 24.6%, respectively. The aforesaid results show that compound 1 can highly reduce *enterovirus* replication in host cells.

EXAMPLE 11

Figure 13:
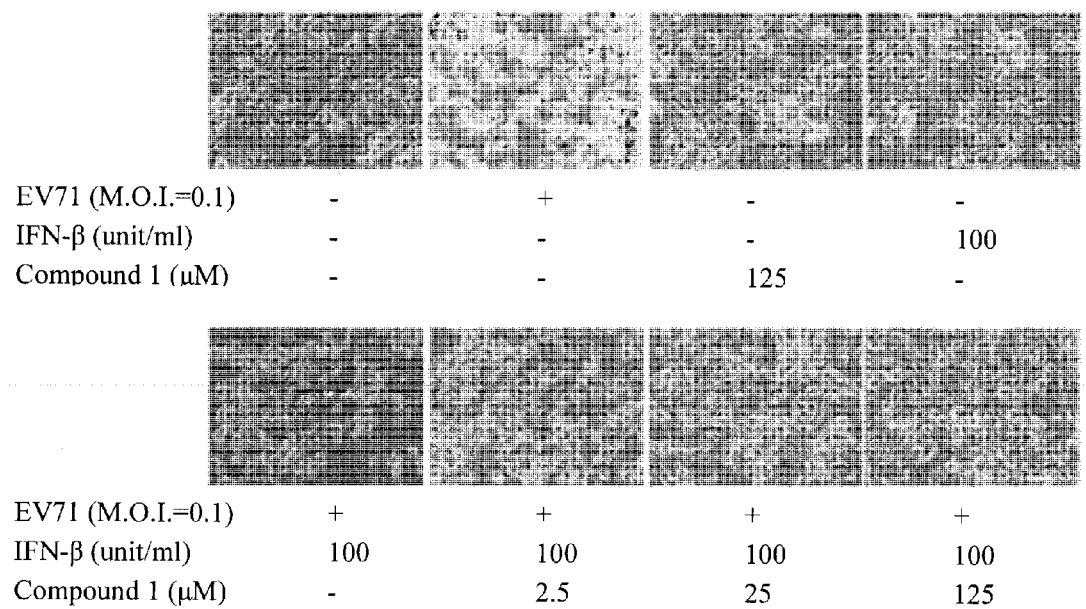
FIG. 13 is a photograph showing a combination of compound (1) and interferon that inhibits the *enterovirus* infection-induced cytopathic effect, wherein the upper row of the horizontal axis represents there is a EV71 infection (+) or not (−); the middle row of the horizontal axis represents the concentration of interferon-β, and the lower row of the horizontal axis represents the concentration of compound (1)

Inhibition of *Enterovirus* Infection-Induced Cytopathic Effect by Using an Interferon Simultaneously The RD cells were cultured in a 24-well culture plate at an initial density of $3\times10^4$ per well with 1 ml of 2% FBS-containing MEM medium per well. The cells were incubated in an incubator (37° C., 5% $CO_2$) overnight. The medium was removed until the cells adhered to the plate. 1 ml of fresh 2% FBS-containing MEM medium was simultaneously added into each well. The RD cells were infected with an EV71 virus strain (M.O.I.=0.1). Different concentrations of compound 1 (final concentrations were 0, 2.5, 25 and 125 μM) and/or IFN-β (final concentrations were 0 and 100 unit/ml) were separately added into different wells. The RD cells were incubated in an incubator (37° C., 5% $CO_2$) for 36 hours, and then their morphology was observed by photography. The results are shown in FIG. 13 and Table 2. In addition, 200 μl of culture medium supernatant was collected from each well and stored at −80° C. for conducting the viral plaque test of Example 12.

As shown in FIG. 13 and Table 2, there was a cytopathic effect in all RD cells infected with EV71 for 36 hours, and the cell survival rate is merely 5.01%. The cytopathic effect would be effectively inhibited by a combination treatment of compound 1 and 100 units/ml of IFN-β. Furthermore, the cell survival rate was increased with the increment of the amount of compound 1. For example, 83.3% of cell survival rate can be provided when the cells were treated with 125 μM of compound 1. The aforesaid results show that a combination of compound (1) and interferon can generate a synergistic effect on inhibiting the *enterovirus* infection-induced cytopathic effect.

TABLE 2

| EV71 (M.O.I. = 0.1) | IFN-β (unit/ml) | Compound 1 (μM) | Cell survival rate (%) |
|---|---|---|---|
| − | − | − | 86.67 |
| + | − | − | 5.01 |

TABLE 2-continued

| EV71 (M.O.I. = 0.1) | IFN-β (unit/ml) | Compound 1 (μM) | Cell survival rate (%) |
|---|---|---|---|
| − | − | 125 | 86.85 |
| − | 100 | − | 87.35 |
| + | 100 | − | 33.1 |
| + | 100 | 2.5 | 46.9 |
| + | 100 | 25 | 55.86 |
| + | 100 | 125 | 83.3 |

EXAMPLE 12

Inhibition of *Enterovirus* Replication by Using an Interferon Simultaneously

The RD cells were cultured in a 24-well culture plate at an initial density of $3 \times 10^4$ per well, as well as with 1 ml of 2% FBS-containing MEM medium per well. The cells were incubated in an incubator (37° C., 5% $CO_2$) overnight. The medium was removed, and then 200 μl of the above $10^4$ times diluted viral medium was added into each well. The cells were infected for 1 hour. Then, 3 ml of 3% agarose covering solution was added into each well. The cells were incubated in an incubator (37° C., 5% $CO_2$) for 3 days. The covering solution was removed. Methyl blue was added into each well. The plate was placed at room temperature overnight, washed with clear water, and dried. The number of plaques was counted to calculate the virus titer and inhibitory rate. The results are shown in FIG. 14.

Figure 14:
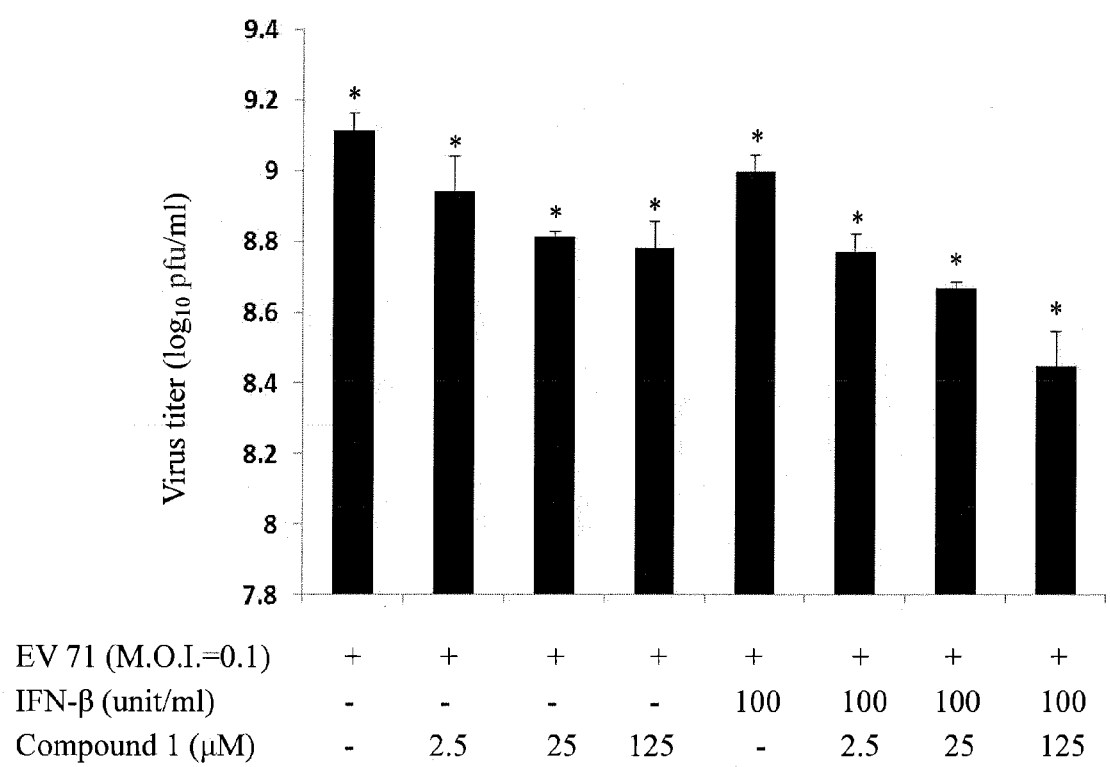
FIG. 14 is a statistical bar diagram showing that the *enterovirus* replication was inhibited by a combination of compound (1) and an interferon (**p<0.001: represents a statistical significance), wherein the vertical axis represents the virus titer, the upper row of the horizontal axis represents there is a EV71 infection (+); the middle row of the horizontal axis represents a concentration of interferon-β, and the lower row of the horizontal axis represents the concentration of compound (1).

As shown in FIG. 14, inhibitory rates of EV 71 replication in RD cells that are caused by a combination of compound 1 (125 μM) and IFN-β (100 unit/ml) was 78% (i.e., 100%× $(10^{9.1}-10^{8.45})/10^{9.1}=78\%$). The result shows that a combination of compound (1) and interferon can generate a synergistic effect on reducing *enterovirus* replication in host cells.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for treating a virus infection in a subject, comprising administering to the subject in need an effective amount of a derivative of aniline selected from the group consisting of a compound of formula (I), a pharmaceutically acceptable salt of the compound of formula (I) combinations thereof:

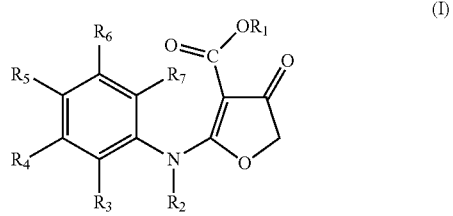

(I)

wherein,
$R_1$ is C1 to C6 alkyl;
$R_2$ is H;
$R_3$, $R_5$, and $R_7$ are independently H, or halogen;
$R_4$ and $R_6$ are independently H, halogen, or C1 to C4 alkyl; and
the virus is at least one of *Flavivirus* genus virus and *Enterovirus* genus virus.

2. The method as claimed in claim 1, wherein the derivative of aniline is ethyl 2-(3',5'-dimethylanilino)-4-oxo-4,5-dihydrofuran-3-carboxylate.

3. The method as claimed in claim 1, wherein the administration results in at least one of activating virus-suppressed Janus kinase-signal transducer and activator of transcription (JAK-STAT) signaling pathway, activating virus-suppressed protein kinase AkT-mammalian target of rapamycin (AkT-mTOR) signaling pathway, activating virus-suppressed extracellular signal-regulated kinase-cAMP response element-binding protein (ERK-CREB) signaling pathway, promoting a virus-infected cell to express an interferon, promoting a virus-infected cell to express an interferon receptor, promoting a virus-infected cell to express an interferon regulatory factor, promoting a virus-infected cell to express protein kinase R (PKR), and promoting a virus-infected cell to express oligoadenylate synthetase (OAS).

4. The method as claimed in claim 3, wherein the interferon is at least one of interferon-α (IFN-α) and interferon-β (IFN-β), the interferon receptor is interferon-α receptor-1 (IFNAR1), and the interferon regulatory factor is at least one of interferon regulatory factor-3 (IRF-3) and interferon regulatory factor-7 (IRF-7).

5. The method as claimed in claim 1 for at least one of inhibiting virus-induced apoptosis, inhibiting virus-induced cytopathic effect, and inhibiting virus replication in a virus-infected cell.

6. The method as claimed in claim 1, wherein the virus is at least one of Japanese encephalitis virus (JEV), dengue virus (DEN), and *enterovirus* type 71 (EV71).

7. The method as claimed in claim 6, wherein the dengue virus is dengue virus type 2 (DEN2).

8. The method as claimed in claim 1, comprising administering to the subject in need an effective amount of the derivative of aniline and an effective amount of an interferon simultaneously or sequentially.

9. The method as claimed in claim 8, wherein the method is for treating *enterovirus* infection and the interferon is at least one of interferon-α (IFN-α) and interferon-β (IFN-β).

10. The method as claimed in claim 8, wherein the method is for treating *enterovirus* type 71 (EV71) infection and the interferon is interferon-β (IFN-β).

11. The method as claimed in claim 2, comprising administering to the subject in need an effective amount of the derivative of aniline and an effective amount of an interferon simultaneously or sequentially.

12. A method for treating *enterovirus* infection, comprising administering to the subject in need an effective amount of ethyl 2-(3',5'-dimethylanilino)-4-oxo-4,5-dihydrofuran-3-carboxylate and an effective amount of an interferon simultaneously or sequentially, wherein the interferon is at least one of interferon-α (IFN-α) and interferon-β (IFN-β).

13. A method for treating *enterovirus* type 71 (EV71) infection, comprising administering to the subject in need an effective amount of ethyl 2-(3',5'-dimethylanilino)-4-oxo-4,5-dihydrofuran-3-carboxylate and an effective amount of interferon-β (IFN-β) simultaneously or sequentially.

* * * * *